US007056889B2

(12) United States Patent
Villanueva et al.

(10) Patent No.: US 7,056,889 B2
(45) Date of Patent: Jun. 6, 2006

(54) COMPOUNDS THAT BIND P2Y$_2$ OR P2Y$_1$ RECEPTORS

(75) Inventors: Julie M. Villanueva, Decatur, GA (US); Stephen Quirk, Alpharetta, GA (US)

(73) Assignee: Kimberly-Clark, Worldwide, Inc., Neenah, WI (US)

( * ) Notice: Subject to any disclaimer, the term of this patent is extended or adjusted under 35 U.S.C. 154(b) by 89 days.

(21) Appl. No.: 10/320,731

(22) Filed: Dec. 16, 2002

(65) Prior Publication Data

US 2004/0116339 A1 Jun. 17, 2004

(51) Int. Cl.
*A61K 31/00* (2006.01)
*A61K 38/00* (2006.01)
*A61K 38/05* (2006.01)

(52) U.S. Cl. ............................ 514/19; 514/23; 514/25; 514/53; 514/274; 514/311; 514/422; 514/425; 514/529; 514/547; 514/562; 514/572; 514/574

(58) Field of Classification Search ................ 514/19, 514/25, 53, 562, 23, 374, 425, 529, 572, 514/574, 311, 422, 542, 547; 560/155, 157, 560/159, 160, 169, 170, 171, 123, 13, 110, 560/129; 536/4.1, 123, 13, 1.11, 120; 562/556, 562/432, 509; 544/302; 548/496, 542, 544, 548/520; 546/169
See application file for complete search history.

(56) References Cited

U.S. PATENT DOCUMENTS

| 5,789,391 | A | 8/1998 | Jacobus et al. ............... 514/51 |
| 5,837,861 | A | 11/1998 | Pendergast et al. ........ 536/25.6 |
| 5,958,897 | A | 9/1999 | Jacobus et al. ............... 514/49 |
| 5,972,904 | A | 10/1999 | Jacobus et al. ............... 514/51 |
| 5,981,506 | A | 11/1999 | Jacobus et al. ............... 514/47 |
| 5,985,849 | A | 11/1999 | Kindon et al. ............... 514/51 |
| 6,107,091 | A | 8/2000 | Cowsert ..................... 435/375 |
| 6,107,297 | A | 8/2000 | Kindon et al. ......... 514/252.02 |
| 6,200,981 | B1 | 3/2001 | Kindon et al. ............... 514/269 |
| 6,264,975 | B1 | 7/2001 | Boucher, Jr. ................ 424/434 |
| 6,277,855 | B1 | 8/2001 | Yerxa ......................... 514/256 |
| 6,331,529 | B1 | 12/2001 | Yerxa et al. .................. 514/47 |
| 6,436,910 | B1 | 8/2002 | Yerxa et al. .................. 514/47 |
| 6,444,115 | B1 | 9/2002 | Hodges et al. ............... 205/792 |
| 6,462,028 | B1 | 10/2002 | Pendergast et al. ........... 514/47 |
| 6,475,360 | B1 | 11/2002 | Hodges et al. ......... 204/403.14 |
| 2003/0129157 | A1* | 7/2003 | Sonneville-Aubrun et al. ..................... 424/470.31 |
| 2003/0176358 | A1* | 9/2003 | Egawa et al. ................. 514/18 |

FOREIGN PATENT DOCUMENTS

EP 1 023 836 A1 * 8/2000
WO WO 96/27370 A1 * 9/1996

OTHER PUBLICATIONS

Bouchie, Julie L., et al., "P2Y Receptor Regulation of PAI-1 Expression in Vascular Smooth Muscle Cells", *Arteriosclerosis, Thrombosis, and Vascular Biology*, (Mar., 2000),866-873.

Garrad, Richard C., et al., "Structural Basis of Agonist-induced Desensitization and Sequestration of the P2Y2 Nucleotide Receptor", *The Journal of Biological Chemistry*, 273 (45), (Nov., 1998),29437-29444.

Gorodeski, George I., "Expression, Regalation, and Function of P2X4 Purinergic Receptor in Human Cervical Epithelial Cells", *American Journal of Physiology-Cell Physiology*, 282, (2002),C84-C93.

Gorodeski, George I., et al., "Regulation by Retinoids of P2Y2 Nucleotide Receptor mRNA in Human Uterine Cervical Cells", *American Journal of Physiology*, 275, (1998), C758-C765.

Gorodeski, George I., et al., "Regulation of the Paracellular Permeability of Cultured Human Cervical Epithelium by a Nucleotide Receptor", *J. Soc. Gynecol. Invest*, 2 (5), (Sep.-Oct., 1995),716-720.

Gorodeski, George I., "Regulation of Transcervical Permeability by Two Distinct P2 Purinergic Receptor Mechanisms", *American Journal of Physiology-Cell Physiology*, 282, (2002),C75-C83.

Insel, Paul A., et al., "P2Y Receptors of MDCK Cells: Epithelial Cell Regulation by Extracellular Nucleotides", *Clinical and Experimental Pharmacology and Physiology*, 28, (2001),351-354.

Jumblatt, James E., et al., "Regulation of Ocular Mucin Secretion by P2Y2 Nucleotide Receptors in Rabbit and Human Conjunctiva", *Experimental Eye Research*, 67, (1998),341-346.

Santiago-Perez, Laura I., et al., "P2Y2 Nucleotide Receptor Signaling in Human Monocytic Cells: Activation, Desensitization, and Coupling ot Mitogen-Activated Protein Kinases", *Journal of Cellular Physiology*, 187, (2001), 196-208.

Velazquez, Betty, et al., "Differential Agonist-induced Desensitization of P2Y2 Nucleotide Receptors by ATP and UTP", *Molecular and Cellular Biochemistry*, 206, (2000),75-89.

Erb, L. , et al., "An RGD Sequence in the P2Y2 Receptor interacts with alpha-v-beta-3 Integrins and is Required for Go-Mediated Signal Transduction", *The Journal of Cell Biology*, 153, (Apr. 30, 2001),491-501.

Insel, P. A., et al., "P2Y Receptors of MDCK Cells: Epithelial Cell Regulation by Extracellular Nucleotides", *Clinical and Experimental Pharmacology and Physiology*, 28, (2001),351-354.

* cited by examiner

*Primary Examiner*—Jeffrey Edwin Russel
(74) *Attorney, Agent, or Firm*—Schwegman, Lundberg, Woessner & Kluth P.A.

(57) ABSTRACT

The invention provides peptides and compounds that can bind to P2Y$_2$ receptors that are useful for modulating the secretion of mucus within mucosal surfaces.

5 Claims, 1 Drawing Sheet

SEQUENCE LISTING

<160> NUMBER OF SEQ ID NOS: 47

<210> SEQ ID NO 1
<211> LENGTH: 11
<212> TYPE: PRT
<213> ORGANISM: Artificial Sequence
<220> FEATURE:
<223> OTHER INFORMATION: Synthetic example of peptide modulator of P2Y2
or P2Y1 receptors

<400> SEQUENCE: 1

Tyr Ala Arg Gly Asp His Trp Pro Phe Ser Thr
 1               5                  10

<210> SEQ ID NO 2
<211> LENGTH: 24
<212> TYPE: PRT
<213> ORGANISM: Artificial Sequence
<220> FEATURE:
<223> OTHER INFORMATION: Synthetic example of peptide modulator of P2Y2
or P2Y1 receptors

<400> SEQUENCE: 2

Ser Val Arg Gly Thr Arg Ile Thr Cys His Asp Thr Ser Ala Arg Glu
 1               5                  10                  15

Leu Phe Ser His Phe Val Ala Tyr
            20

<210> SEQ ID NO 3
<211> LENGTH: 26
<212> TYPE: PRT
<213> ORGANISM: Artificial Sequence
<220> FEATURE:
<223> OTHER INFORMATION: Synthetic example of peptide modulator of P2Y2
or P2Y1 receptors

<400> SEQUENCE: 3

Leu Tyr Tyr Ser Phe Arg Ser Leu Asp Leu Ser Cys His Thr Leu Asn
 1               5                  10                  15

Ala Ile Asn Met Ala Tyr Lys Ile Thr Arg
            20                  25

<210> SEQ ID NO 4
<211> LENGTH: 35
<212> TYPE: PRT
<213> ORGANISM: Artificial Sequence
<220> FEATURE:
<223> OTHER INFORMATION: Synthetic example of peptide modulator of P2Y2
or P2Y1 receptors

<400> SEQUENCE: 4

Ala Ala Ala Asp Leu Glu Pro Trp Asn Ser Thr Ile Asn Cys Thr Trp
 1               5                  10                  15

Glu Leu Asp Glu Leu Cys Tyr Lys Cys Arg Phe Asn Glu Asp Phe Lys
            20                  25                  30

Tyr Val Leu
        35

<210> SEQ ID NO 5
<211> LENGTH: 5
<212> TYPE: PRT
<213> ORGANISM: Artificial Sequence
<220> FEATURE:
<223> OTHER INFORMATION: Synthetic example of peptide modulator of P2Y2 or P2Y1 receptors

<400> SEQUENCE: 5

Ala Ala Ala Ala Glu
1               5

<210> SEQ ID NO 6
<211> LENGTH: 4
<212> TYPE: PRT
<213> ORGANISM: Artificial Sequence
<220> FEATURE:
<223> OTHER INFORMATION: Synthetic example of peptide modulator of P2Y2
                         or P2Y1 receptors

<400> SEQUENCE: 6

Ala Gly Ala Ala
1

<210> SEQ ID NO 7
<211> LENGTH: 6
<212> TYPE: PRT
<213> ORGANISM: Artificial Sequence
<220> FEATURE:
<223> OTHER INFORMATION: Synthetic example of peptide modulator of P2Y2
                         or P2Y1 receptors
<220> FEATURE:
<221> NAME/KEY: SITE
<222> LOCATION: (2)...(6)
<223> OTHER INFORMATION: Xaa = D-Ala

<400> SEQUENCE: 7

Ala Xaa Xaa Xaa Xaa Xaa
1               5

<210> SEQ ID NO 8
<211> LENGTH: 4
<212> TYPE: PRT
<213> ORGANISM: Artificial Sequence
<220> FEATURE:
<223> OTHER INFORMATION: Synthetic example of peptide modulator of P2Y2
                         or P2Y1 receptors

<400> SEQUENCE: 8

Gly Gly Ser Ala
1

<210> SEQ ID NO 9
<211> LENGTH: 3
<212> TYPE: PRT
<213> ORGANISM: Artificial Sequence
<220> FEATURE:
<223> OTHER INFORMATION: Synthetic example of peptide modulator of P2Y2
                         or P2Y1 receptors

<400> SEQUENCE: 9

Gly Gly Gly
1

<210> SEQ ID NO 10
<211> LENGTH: 4
<212> TYPE: PRT
<213> ORGANISM: Artificial Sequence
<220> FEATURE:
<223> OTHER INFORMATION: Synthetic example of peptide modulator of P2Y2
                         or P2Y1 receptors

<400> SEQUENCE: 10

Gly Gly Gly Ala

```
<210> SEQ ID NO 11
<211> LENGTH: 4
<212> TYPE: PRT
<213> ORGANISM: Artificial Sequence
<220> FEATURE:
<223> OTHER INFORMATION: Synthetic example of peptide modulator of P2Y2
      or P2Y1 receptors

<400> SEQUENCE: 11

Gly Gly His Gly
 1

<210> SEQ ID NO 12
<211> LENGTH: 5
<212> TYPE: PRT
<213> ORGANISM: Artificial Sequence
<220> FEATURE:
<223> OTHER INFORMATION: Synthetic example of peptide modulator of P2Y2
      or P2Y1 receptors
<220> FEATURE:
<221> NAME/KEY: SITE
<222> LOCATION: 4
<223> OTHER INFORMATION: Xaa = D-Ala

<400> SEQUENCE: 12

Gly Ala Ala Xaa Ala
 1               5

<210> SEQ ID NO 13
<211> LENGTH: 4
<212> TYPE: PRT
<213> ORGANISM: Artificial Sequence
<220> FEATURE:
<223> OTHER INFORMATION: Synthetic example of peptide modulator of P2Y2
      or P2Y1 receptors

<400> SEQUENCE: 13

Gly Gly Ala Gly
 1

<210> SEQ ID NO 14
<211> LENGTH: 3
<212> TYPE: PRT
<213> ORGANISM: Artificial Sequence
<220> FEATURE:
<223> OTHER INFORMATION: Synthetic example of peptide modulator of P2Y2
      or P2Y1 receptors

<400> SEQUENCE: 14

Gly Ala Ala
 1

<210> SEQ ID NO 15
<211> LENGTH: 3
<212> TYPE: PRT
<213> ORGANISM: Artificial Sequence
<220> FEATURE:
<223> OTHER INFORMATION: Synthetic example of peptide modulator of P2Y2
      or P2Y1 receptors

<400> SEQUENCE: 15

Ser Glu Gly
 1

<210> SEQ ID NO 16
<211> LENGTH: 4
```

```
<212> TYPE: PRT
<213> ORGANISM: Artificial Sequence
<220> FEATURE:
<223> OTHER INFORMATION: Synthetic example of peptide modulator of P2Y2
                        or P2Y1 receptors

<400> SEQUENCE: 16

Gly Gly Glu Ala
1

<210> SEQ ID NO 17
<211> LENGTH: 3
<212> TYPE: PRT
<213> ORGANISM: Artificial Sequence
<220> FEATURE:
<223> OTHER INFORMATION: Synthetic example of peptide modulator of P2Y2
                        or P2Y1 receptors

<400> SEQUENCE: 17

Glu His Gly
1

<210> SEQ ID NO 18
<211> LENGTH: 3
<212> TYPE: PRT
<213> ORGANISM: Artificial Sequence
<220> FEATURE:
<223> OTHER INFORMATION: Synthetic example of peptide modulator of P2Y2
                        or P2Y1 receptors

<400> SEQUENCE: 18

Gly Ala Asn
1

<210> SEQ ID NO 19
<211> LENGTH: 4
<212> TYPE: PRT
<213> ORGANISM: Artificial Sequence
<220> FEATURE:
<223> OTHER INFORMATION: Synthetic example of peptide modulator of P2Y2
                        or P2Y1 receptors

<400> SEQUENCE: 19

Ala Ala Ala Pro
1

<210> SEQ ID NO 20
<211> LENGTH: 4
<212> TYPE: PRT
<213> ORGANISM: Artificial Sequence
<220> FEATURE:
<223> OTHER INFORMATION: Synthetic example of peptide modulator of P2Y2
                        or P2Y1 receptors
<220> FEATURE:
<221> NAME/KEY: SITE
<222> LOCATION: 1
<223> OTHER INFORMATION: Xaa = D-Ala

<400> SEQUENCE: 20

Xaa Ala Ala Ala
1

<210> SEQ ID NO 21
<211> LENGTH: 3
<212> TYPE: PRT
<213> ORGANISM: Artificial Sequence
<220> FEATURE:
<223> OTHER INFORMATION: Synthetic example of peptide modulator of P2Y2
                        or P2Y1 receptors
```

```
<400> SEQUENCE: 21

His Gly Gly
 1

<210> SEQ ID NO 22
<211> LENGTH: 2
<212> TYPE: PRT
<213> ORGANISM: Artificial Sequence
<220> FEATURE:
<223> OTHER INFORMATION: Synthetic example of peptide modulator of P2Y2
                        or P2Y1 receptors
<220> FEATURE:
<221> NAME/KEY: SITE
<222> LOCATION: 1
<223> OTHER INFORMATION: Xaa = D-Glu

<400> SEQUENCE: 22

Xaa Glu
 1

<210> SEQ ID NO 23
<211> LENGTH: 4
<212> TYPE: PRT
<213> ORGANISM: Artificial Sequence
<220> FEATURE:
<223> OTHER INFORMATION: Synthetic example of peptide modulator of P2Y2
                        or P2Y1 receptors

<400> SEQUENCE: 23

Gly Gly His Ala
 1

<210> SEQ ID NO 24
<211> LENGTH: 3
<212> TYPE: PRT
<213> ORGANISM: Artificial Sequence
<220> FEATURE:
<223> OTHER INFORMATION: Synthetic example of peptide modulator of P2Y2
                        or P2Y1 receptors

<400> SEQUENCE: 24

Lys Gly Glu
 1

<210> SEQ ID NO 25
<211> LENGTH: 2
<212> TYPE: PRT
<213> ORGANISM: Artificial Sequence
<220> FEATURE:
<223> OTHER INFORMATION: Synthetic example of peptide modulator of P2Y2
                        or P2Y1 receptors
<220> FEATURE:
<221> NAME/KEY: SITE
<222> LOCATION: (1)...(2)
<223> OTHER INFORMATION: Xaa = D-Glu

<400> SEQUENCE: 25

Xaa Xaa
 1

<210> SEQ ID NO 26
<211> LENGTH: 3
<212> TYPE: PRT
<213> ORGANISM: Artificial Sequence
<220> FEATURE:
<223> OTHER INFORMATION: Synthetic example of peptide modulator of P2Y2
                        or P2Y1 receptors
```

```
<400> SEQUENCE: 26

Gly Pro Ala
 1

<210> SEQ ID NO 27
<211> LENGTH: 3
<212> TYPE: PRT
<213> ORGANISM: Artificial Sequence
<220> FEATURE:
<223> OTHER INFORMATION: Synthetic example of peptide modulator of P2Y2
                        or P2Y1 receptors

<400> SEQUENCE: 27

Ala Ala Tyr
 1

<210> SEQ ID NO 28
<211> LENGTH: 3
<212> TYPE: PRT
<213> ORGANISM: Artificial Sequence
<220> FEATURE:
<223> OTHER INFORMATION: Synthetic example of peptide modulator of P2Y2
                        or P2Y1 receptors
<220> FEATURE:
<221> NAME/KEY: SITE
<222> LOCATION: 3
<223> OTHER INFORMATION: Xaa = Asp-OH

<400> SEQUENCE: 28

Glu Glu Xaa
 1

<210> SEQ ID NO 29
<211> LENGTH: 4
<212> TYPE: PRT
<213> ORGANISM: Artificial Sequence
<220> FEATURE:
<223> OTHER INFORMATION: Synthetic example of peptide modulator of P2Y2
                        or P2Y1 receptors
<220> FEATURE:
<221> NAME/KEY: SITE
<222> LOCATION: 3
<223> OTHER INFORMATION: Xaa = beta-Ala

<400> SEQUENCE: 29

Gly Gly Xaa Gly
 1

<210> SEQ ID NO 30
<211> LENGTH: 5
<212> TYPE: PRT
<213> ORGANISM: Artificial Sequence
<220> FEATURE:
<223> OTHER INFORMATION: Synthetic example of peptide modulator of P2Y2
                        or P2Y1 receptors

<400> SEQUENCE: 30

Asp Ala Ser Gly Glu
 1               5

<210> SEQ ID NO 31
<211> LENGTH: 3
<212> TYPE: PRT
<213> ORGANISM: Artificial Sequence
<220> FEATURE:
<223> OTHER INFORMATION: Synthetic example of peptide modulator of P2Y2
                        or P2Y1 receptors

<400> SEQUENCE: 31
```

Glu Glu Gln
1

<210> SEQ ID NO 32
<211> LENGTH: 4
<212> TYPE: PRT
<213> ORGANISM: Artificial Sequence
<220> FEATURE:
<223> OTHER INFORMATION: Synthetic example of peptide modulator of P2Y2
      or P2Y1 receptors

<400> SEQUENCE: 32

Ala Ala Pro Ala
1

<210> SEQ ID NO 33
<211> LENGTH: 4
<212> TYPE: PRT
<213> ORGANISM: Artificial Sequence
<220> FEATURE:
<223> OTHER INFORMATION: Synthetic example of peptide modulator of P2Y2
      or P2Y1 receptors

<400> SEQUENCE: 33

Gly Gly Tyr Ala
1

<210> SEQ ID NO 34
<211> LENGTH: 4
<212> TYPE: PRT
<213> ORGANISM: Artificial Sequence
<220> FEATURE:
<223> OTHER INFORMATION: Synthetic example of peptide modulator of P2Y2
      or P2Y1 receptors

<400> SEQUENCE: 34

Trp Gly Gly Tyr
1

<210> SEQ ID NO 35
<211> LENGTH: 2
<212> TYPE: PRT
<213> ORGANISM: Artificial Sequence
<220> FEATURE:
<223> OTHER INFORMATION: A Synthetic modified peptide
<220> FEATURE:
<221> NAME/KEY: SITE
<222> LOCATION: 1
<223> OTHER INFORMATION: Xaa = Glycyl-Ala

<400> SEQUENCE: 35

Xaa Gln
1

<210> SEQ ID NO 36
<211> LENGTH: 1
<212> TYPE: PRT
<213> ORGANISM: Artificial Sequence
<220> FEATURE:
<223> OTHER INFORMATION: A synthetic modified peptide
<220> FEATURE:
<221> NAME/KEY: SITE
<222> LOCATION: 1
<223> OTHER INFORMATION: Xaa = S-nitrosoglutathione

<400> SEQUENCE: 36

Xaa
1

```
<210> SEQ ID NO 37
<211> LENGTH: 1
<212> TYPE: PRT
<213> ORGANISM: Artificial Sequence
<220> FEATURE:
<223> OTHER INFORMATION: A synthetic modified peptide
<220> FEATURE:
<221> NAME/KEY: SITE
<222> LOCATION: 1
<223> OTHER INFORMATION: Xaa = Glutathione-monoisopropyl-ester (reduced)

<400> SEQUENCE: 37

Xaa
 1

<210> SEQ ID NO 38
<211> LENGTH: 2
<212> TYPE: PRT
<213> ORGANISM: Artificial Sequence
<220> FEATURE:
<223> OTHER INFORMATION: A synthetic modified peptide
<220> FEATURE:
<221> NAME/KEY: SITE
<222> LOCATION: 1
<223> OTHER INFORMATION: Xaa = L-Cystinyl

<400> SEQUENCE: 38

Xaa Cys
 1

<210> SEQ ID NO 39
<211> LENGTH: 4
<212> TYPE: PRT
<213> ORGANISM: Artificial Sequence
<220> FEATURE:
<223> OTHER INFORMATION: A synthetic modified peptide
<220> FEATURE:
<221> NAME/KEY: SITE
<222> LOCATION: 1
<223> OTHER INFORMATION: Xaa = Ac-His

<400> SEQUENCE: 39

Xaa His Gly His
 1

<210> SEQ ID NO 40
<211> LENGTH: 2
<212> TYPE: PRT
<213> ORGANISM: Artificial Sequence
<220> FEATURE:
<223> OTHER INFORMATION: A synthetic modified peptide
<220> FEATURE:
<221> NAME/KEY: SITE
<222> LOCATION: 2
<223> OTHER INFORMATION: Xaa = Ala-NH2

<400> SEQUENCE: 40

Gly Xaa
 1

<210> SEQ ID NO 41
<211> LENGTH: 2
<212> TYPE: PRT
<213> ORGANISM: Artificial Sequence
<220> FEATURE:
<223> OTHER INFORMATION: A synthetic modified peptide
<220> FEATURE:
<221> NAME/KEY: SITE
<222> LOCATION: 1
```

<223> OTHER INFORMATION: Xaa = Ac-Glycyl

<400> SEQUENCE: 41

Xaa Glu
1

<210> SEQ ID NO 42
<211> LENGTH: 2
<212> TYPE: PRT
<213> ORGANISM: Artificial Sequence
<220> FEATURE:
<223> OTHER INFORMATION: A synthetic modified peptide
<220> FEATURE:
<221> NAME/KEY: SITE
<222> LOCATION: 1
<223> OTHER INFORMATION: Xaa = Methoxycarbonyl-Phe

<400> SEQUENCE: 42

Xaa Gly
1

<210> SEQ ID NO 43
<211> LENGTH: 4
<212> TYPE: PRT
<213> ORGANISM: Artificial Sequence
<220> FEATURE:
<223> OTHER INFORMATION: A synthetic modified peptide
<220> FEATURE:
<221> NAME/KEY: SITE
<222> LOCATION: 1
<223> OTHER INFORMATION: Xaa = 3-5-Diiodo-D-Tyr

<400> SEQUENCE: 43

Xaa Ala Gly Gly
1

<210> SEQ ID NO 44
<211> LENGTH: 11
<212> TYPE: PRT
<213> ORGANISM: Artificial Sequence
<220> FEATURE:
<223> OTHER INFORMATION: A synthetic example of a peptide which can bind
                        P2Y2 or P2Y1 receptors
<220> FEATURE:
<221> NAME/KEY: SITE
<222> LOCATION: 3, 6
<223> OTHER INFORMATION: Xaa = any basic amino acid
<220> FEATURE:
<221> NAME/KEY: SITE
<222> LOCATION: 4, 8
<223> OTHER INFORMATION: Xaa = any apolar amino acid
<220> FEATURE:
<221> NAME/KEY: SITE
<222> LOCATION: 7, 9
<223> OTHER INFORMATION: Xaa = any aromatic amino acid
<220> FEATURE:
<221> NAME/KEY: SITE
<222> LOCATION: 10, 11
<223> OTHER INFORMATION: any polar amino acid
<220> FEATURE:
<221> NAME/KEY: SITE
<222> LOCATION: 1
<223> OTHER INFORMATION: Xaa = any aromatic or polar amino acid
<220> FEATURE:
<221> NAME/KEY: SITE
<222> LOCATION: (2)...(2)
<223> OTHER INFORMATION: Xaa = any aliphatic amino acid
<220> FEATURE:
<221> NAME/KEY: SITE
<222> LOCATION: (5)...(5)
<223> OTHER INFORMATION: Xaa = any acidic amino acid

<400> SEQUENCE: 44

Xaa Xaa Xaa Xaa Xaa Xaa Xaa Xaa Xaa Xaa Xaa
1               5                   10

<210> SEQ ID NO 45
<211> LENGTH: 24
<212> TYPE: PRT
<213> ORGANISM: Artificial Sequence
<220> FEATURE:
<223> OTHER INFORMATION: A synthetic example of a peptide which can bind
      P2Y2 or P2Y1 receptors
<220> FEATURE:
<221> NAME/KEY: SITE
<222> LOCATION: 1, 5, 8, 12-13, 19
<223> OTHER INFORMATION: Xaa = any polar amino acid
<220> FEATURE:
<221> NAME/KEY: SITE
<222> LOCATION: 2, 7, 14, 17, 22-23
<223> OTHER INFORMATION: Xaa = any aliphatic amino acid
<220> FEATURE:
<221> NAME/KEY: SITE
<222> LOCATION: 3, 6, 10, 15, 21
<223> OTHER INFORMATION: Xaa = any basic amino acid
<220> FEATURE:
<221> NAME/KEY: SITE
<222> LOCATION: 18, 21
<223> OTHER INFORMATION: Xaa = any aromatic amino acid
<220> FEATURE:
<221> NAME/KEY: SITE
<222> LOCATION: 11, 16
<223> OTHER INFORMATION: Xaa = any acidic amino acid
<220> FEATURE:
<221> NAME/KEY: SITE
<222> LOCATION: (4)...(4)
<223> OTHER INFORMATION: Xaa = any apolar amino acid
<220> FEATURE:
<221> NAME/KEY: SITE
<222> LOCATION: (9)...(9)
<223> OTHER INFORMATION: Xaa = any cysteine-like amino acid
<220> FEATURE:
<221> NAME/KEY: SITE
<222> LOCATION: (24)...(24)
<223> OTHER INFORMATION: Xaa = any aromatic or polar amino acid

<400> SEQUENCE: 45

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 46
<211> LENGTH: 26
<212> TYPE: PRT
<213> ORGANISM: Artificial Sequence
<220> FEATURE:
<223> OTHER INFORMATION: A synthetic example of a peptide which can bind
      P2Y2 or P2Y1 receptors
<220> FEATURE:
<221> NAME/KEY: SITE
<222> LOCATION: 1, 8, 10, 14-15, 17-18, 21, 24
<223> OTHER INFORMATION: Xaa = any aliphatic amino acid
<220> FEATURE:
<221> NAME/KEY: SITE
<222> LOCATION: 4, 7, 11, 14, 16, 19, 25
<223> OTHER INFORMATION: Xaa = any polar amino acid
<220> FEATURE:
<221> NAME/KEY: SITE
<222> LOCATION: 2-3, 22
<223> OTHER INFORMATION: Xaa = any aromatic or polar amino acid
<220> FEATURE:
<221> NAME/KEY: SITE
<222> LOCATION: 5
<223> OTHER INFORMATION: Xaa = any aromatic amino acid
<220> FEATURE:
<221> NAME/KEY: SITE

```
<222> LOCATION: 6, 13, 23, 26
<223> OTHER INFORMATION: Xaa = any basic amino acid
<220> FEATURE:
<221> NAME/KEY: SITE
<222> LOCATION: (9)...(9)
<223> OTHER INFORMATION: Xaa = any acidic amino acid
<220> FEATURE:
<221> NAME/KEY: SITE
<222> LOCATION: (12)...(12)
<223> OTHER INFORMATION: Xaa = any cysteine-like amino acid
<220> FEATURE:
<221> NAME/KEY: SITE
<222> LOCATION: (20)...(20)
<223> OTHER INFORMATION: Xaa = any apolar amino acid

<400> SEQUENCE: 46

Xaa Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa
            20                  25

<210> SEQ ID NO 47
<211> LENGTH: 35
<212> TYPE: PRT
<213> ORGANISM: Artificial Sequence
<220> FEATURE:
<223> OTHER INFORMATION: A synthetic example of a peptide which can bind
                        P2Y2 or P2Y1 receptors
<220> FEATURE:
<221> NAME/KEY: SITE
<222> LOCATION: 1-3, 5, 12, 18, 21, 34-35
<223> OTHER INFORMATION: Xaa = any aliphatic amino acid
<220> FEATURE:
<221> NAME/KEY: SITE
<222> LOCATION: 4, 6, 17, 19-20, 29-30
<223> OTHER INFORMATION: Xaa = any acidic amino acid
<220> FEATURE:
<221> NAME/KEY: SITE
<222> LOCATION: 8, 16, 27, 31
<223> OTHER INFORMATION: Xaa = any aromatic amino acid
<220> FEATURE:
<221> NAME/KEY: SITE
<222> LOCATION: 9-11, 13, 15, 28
<223> OTHER INFORMATION: Xaa = any polar amino acid
<220> FEATURE:
<221> NAME/KEY: SITE
<222> LOCATION: 14, 22, 45
<223> OTHER INFORMATION: Xaa = any cysteine-like amino acid
<220> FEATURE:
<221> NAME/KEY: SITE
<222> LOCATION: (7)...(7)
<223> OTHER INFORMATION: Xaa = any apolar amino acid
<220> FEATURE:
<221> NAME/KEY: SITE
<222> LOCATION: (23)...(23)
<223> OTHER INFORMATION: Xaa = any aromatic or polar amino acid
<220> FEATURE:
<221> NAME/KEY: SITE
<222> LOCATION: (33)...(33)
<223> OTHER INFORMATION: Xaa = any aromatic or polar amino acid
<220> FEATURE:
<221> NAME/KEY: SITE
<222> LOCATION: (24)...(24)
<223> OTHER INFORMATION: Xaa = any basic amino acid
<220> FEATURE:
<221> NAME/KEY: SITE
<222> LOCATION: (26)...(26)
<223> OTHER INFORMATION: Xaa = any basic amino acid
<220> FEATURE:
<221> NAME/KEY: SITE
<222> LOCATION: (32)...(32)
<223> OTHER INFORMATION: Xaa = any basic amino acid
```

-continued

```
<400> SEQUENCE: 47

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa
        35
```

COMPOUNDS THAT BIND P2Y$_2$ OR P2Y$_1$ RECEPTORS

FIELD OF THE INVENTION

The present invention relates to the use of compounds that can bind and modulate the activity of P2Y$_2$ or P2Y$_1$ receptors. Such compounds are useful for increasing secretion of mucus from mucosal surfaces.

BACKGROUND OF THE INVENTION

Chronic obstructive pulmonary disease (COPD) affects 15 million patients in the U.S. and is the sixth leading cause of death. It is characterized by the retention of mucus secretions in the lungs. Many patients diagnosed with COPD have a disorder called chronic bronchitis (CB), and 600,000 patients are hospitalized each year due to an acute exacerbation of CB. Cystic fibrosis and Primary Ciliary Dyskinesia (PCD) are other examples of lung disorders that have a clinical profile similar to COPD. Ciliary dyskinesia, whether primary or secondary, results in retained secretions that can only be cleared by coughing.

Another disease state characterized by the accumulation of retained mucous secretions is sinusitis. Sinusitis is an inflammation of the paranasal sinuses typically associated with an upper respiratory infection. It is this country's most common health-care complaint, affecting an estimated 31 million people. (A. Moss and V. Parsons, National Center for Health Statistics, 1986: 66–7, DHHS Publication No. (PHS) 86-1588 (1985)).

Otitis media (OM) is a viral or bacterial infection of the middle ear that primarily afflicts children under the age of three. It is usually precipitated by an upper respiratory infection that spreads into the middle ear via the nasopharynx and eustachian tube. Approximately 25–50 million office visits are made each year for diagnosis and treatment of OM. By age three, about 75% of children will have had at least one episode of acute OM (J. Klein, Clin. Infect. Dis. 19, 823–33 (1994)). Following appropriate treatment with antibiotics, accumulated fluid in the middle ear remains, causing hearing impairment and potential language and cognitive development delays. Enhanced ability to clear secretions in the middle ear would reduce or eliminate significant sequelae of otitis media.

An additional disorder resulting from retained secretions is pneumonia. Patients who are immobilized for a variety of reasons are at high risk for developing pneumonia. Despite extra vigilance and numerous interventions, pneumonia develops in over 400,000 patients per year, with significant morbidity and mortality.

There are also situations where it is therapeutically desirable to increase drainage of the lacrimal system. When the lacrimal drainage system is not functioning properly the result can be excessive tearing (epiphora), mucopurulent discharge, and recurrent dacryocystitis. Current treatments for nasolacrimal duct obstruction are mostly invasive surgical procedures, and researchers have sought to discover noninvasive pharmaceutical treatments.

Tear secretion can be stimulated from lacrimal accessory tissues via P2Y$_2$ and/or P2Y$_4$ purinergic receptor-mediated mechanisms similar to those which hydrate airway epithelia. Dry eye disease is the general term for indications produced by abnormalities of the precorneal tear film characterized by a decrease in tear production or an increase in tear film evaporation, together with the ocular surface disease that results. Currently, the pharmaceutical treatment of dry eye disease is mostly limited to administration of artificial tears (saline solution) to temporarily rehydrate the eyes. However, relief is short lived and frequent dosing is necessary.

Secretory functions of the uterine, cervical and vaginal mucous cells have a profound impact on the function and health of the reproductive tract. For example, the quality and quantity of cervical mucus changes throughout the menstrual cycle and such changes dramatically influence fertility. Under the influence of rising estrogen levels, cervical mucus becomes thin, allowing the passage of spermatozoa. Later in the menstrual cycle, as progesterone levels increase, mucus becomes thick and hostile to sperm penetration, thereby closing the window of fertility. Such thickening of cervical mucus is thought to be one of the primary modes of contraceptive action for progestin-only contraceptives.

Estrogen stimulates the production of thin, isotonic mucus, with increased amounts of high molecular weight glycoproteins. Cervical mucus contains 98% water at mid cycle and 90% at other times. Cervical mucus is also rich in metallic ions, enzymes (such as alkaline phosphatase, etc.), soluble proteins and salts. The gel phase of cervical mucus contains high molecular weight glycoproteins called mucin. Mucin micelles cross-link by disulfide bridges. Estrogen and progesterone control the arrangement of these micelles. These micellar arrangements influence the rheological properties of mucus. See Kopito et al. *Water and electrolytes in human cervical mucus*. Fertil. Steril. 1973;24:499–506; Fordney-Settlage, D. *A review of cervical mucus and sperm interactions in humans*. Int. J. Fertil. 1981;26:161–169.

As estrogen levels fall during menopause, estrogen dependent tissue will start to involute and take on the characteristic appearance of estrogen deprivation. Cervical mucus levels diminish and vaginal mucosa regresses during menopause. With aging, the vagina becomes shortened, ruggae disappear, and elasticity is lost. Vaginal secretions become scanty. When estrogen is provided, some of these effects are reversed: the cervix starts to secrete some mucus and the vaginal mucosa regains its lost layers. However, the symptoms do not disappear completely, in part because the amount of estrogen provided for hormone replacement is lower than circulating estrogen levels during a normal menstrual cycle.

Approximately 40% of postmenopausal women experience atrophic vaginitis or vaginal dryness. During vaginal atrophy, the vaginal epithelium decreases in thickness, hydration, ruggae (folds), and blood flow. Causes of atrophic vaginitis include a decrease in the amount of estrogen present both locally and systemically as well as environmental factors such as chemotherapy, antihistamines, smoking cigarettes, excessive exercise, and vaginal products (i.e. douches, deodorants, and perfumes).

Estrogens or hormone replacement therapies cab be effective in reducing vaginal dryness. However, possible dangerous side effects include higher incidences of breast cancer, endometrial cancer, blood clots, nausea, breast tenderness, and headache. Products that are available over-the-counter include lubricants such as Astroglide and KY Lubricating Jelly as well as moisturizers such as Replens and KY Long Lasting Moisturizer. These products, which are mostly water in composition, provide only temporary relief (1–2 days) for symptoms and provide virtually no long-term benefits to the vaginal tissue.

Therefore, a need exists for new compositions and methods for modulating mucus production at mucosal surfaces.

SUMMARY OF THE INVENTION

The invention provides compositions and methods for modulating mucus production from a variety of mucosal surfaces. Such mucosal surfaces include, for example, the mucosal surfaces of the lungs, throat, sinuses, nasal passages, ear canals, eyes and female reproductive tract.

The invention also provides non-hormonal therapies for vaginal problems such as atrophic vaginitis. In general the benefits of these therapies include minimal side effects, perform their functions by natural mechanisms, and maintain or restore healthy reproductive tissue function.

The invention therefore provides a composition comprising an effective amount of peptide that can bind a $P2Y_2$ or $P2Y_1$ receptor and a pharmaceutically acceptable excipient, wherein the peptide comprises any one of SEQ ID NO:1–47.

The invention also provides a composition comprising an effective amount of a compound that can bind a $P2Y_2$ or $P2Y_1$ and a pharmaceutically acceptable excipient, wherein the compound comprises p-nitrobenzyloxycarbonyloxysuccinimide; 1-benzyl-2-2-5-dioxotetrahydro-1H-pyrrol-1-yl-pyrrolidine-1-2-dicarboxylate; 5-(3-methoxycarbonylacryloyl)isophthalic acid dimethyl ester; 6-O-β-glucopyranosyl-β-D-glucose; cyclobutane-1-2-3-4-tetracarboxylic acid dimethyl ester; mono-2-acryloyloxyethyl-succinate; 2-benzyloxycarbonylamino-3-methylbutyric acid, 2-5-dioxo-pyrrolidin-1-yl-ester; tris(trichlorosilylethyl)methylsilane; 2-5-dioxotetrahydro-1H-pyrrol-1-yl-2-benzyloxycarbonylamino-3-phenylpropane; 2-chloroethylcarbamic acid, 2-5-dioxo-pyrrolidin-1-yl ester; mono-2-methacryloyloxyethyl-succinate; galactosyl diglyceride; 3-beta-hydroxy-5-alpha-androstan-17-one-beta-D-glucoside; N-4-5-dimethoxy-2-nitrobenzyloxycarbonyl-L-tryptophan; 2-amino-2-4-chlorobenzoyloxyiminoethyl-pivalate; disuccinimidyl sebacate; 2-2-2-trichloro-1-2-methoxy-phenylamino-ethyl-carbamic-acid-benzyl-ester; 2-acetamido-2-deoxy-6-O-beta-D-galactopyranosyl-D-galactopyranose; 2-benzyloxycarbonylamino-3-hydroxy-propionylaminoacetic acid ethyl ester; 2-benzyloxycarbonylmethylsulfanyl-6-hydroxy-pyrimidine-4-carboxylic-acid-methyl-ester; 3-(2-2-2-trichloro-1-isobutyrylamino) ethylthioureidobenzoic acid; ester of 2-diazo-1-naphthol-5-sulphone with 2-3-4-trihydroxybenzophenone; 4-5-dihydroxy-6-hydroxymethyl-2-methoxy-4H-pyran-3-yl-carbamic acid benzyl ester; diethyl-trans-1-2-cyclopropanedicarboxylate; allyloxycarbonylmethylsulfanyl-6-hydroxy-pyrimidine-4-carboxylic acid methyl ester; 1-O-alpha-D-glucopyranosyl-D-fructose; methyl-2-2-4-chlorophenylsulfonylamino-acetylamino-2-phenylacetate; N-(2-hydroxy-4-oxo-4-phenylbut-2-enoyl)-2-methylquinoline-4-carbohydrazide; or DL-Djenkolic-acid.

The composition can, for example, be provided as a tablet, capsule, aerosol, solution, lotion, cream, gel, spray, inhaler, foam or vaginal insert. In some embodiments, the composition is administrated by inhalation or by use of a nebulizer.

The composition can be used to modulate the amount, viscosity or retention of mucus by a mucosal surface.

The invention further provides a method for modulating the activity of a $P2Y_2$ or $P2Y_1$ receptor in a mucosal surface of a mammal comprising administering to the mammal a composition comprising an effective amount of a peptide or compound of the invention that can bind a $P2Y_2$ or $P2Y_1$ receptor and a pharmaceutically acceptable excipient.

In another embodiment, the invention provides a method of preventing or treating vaginal dryness in a mammal in need of such prevention or treatment comprising administering to the vaginal cavity an effective amount of a composition comprising a peptide or compound of the invention that can bind a $P2Y_2$ or $P2Y_1$ receptor and a pharmaceutically acceptable excipient for use in the vaginal cavity area.

The invention further provides a method for treating cystic fibrosis in a mammal by modulating the activity of a $P2Y_2$ or $P2Y_1$ receptor in mucosal surfaces of the lung comprising administering to the mammal a composition comprising an effective amount of a peptide or compound of the invention that can bind a $P2Y_2$ or $P2Y_1$ receptor and a pharmaceutically acceptable excipient.

DETAILED DESCRIPTION OF THE INVENTION

Figure 1:
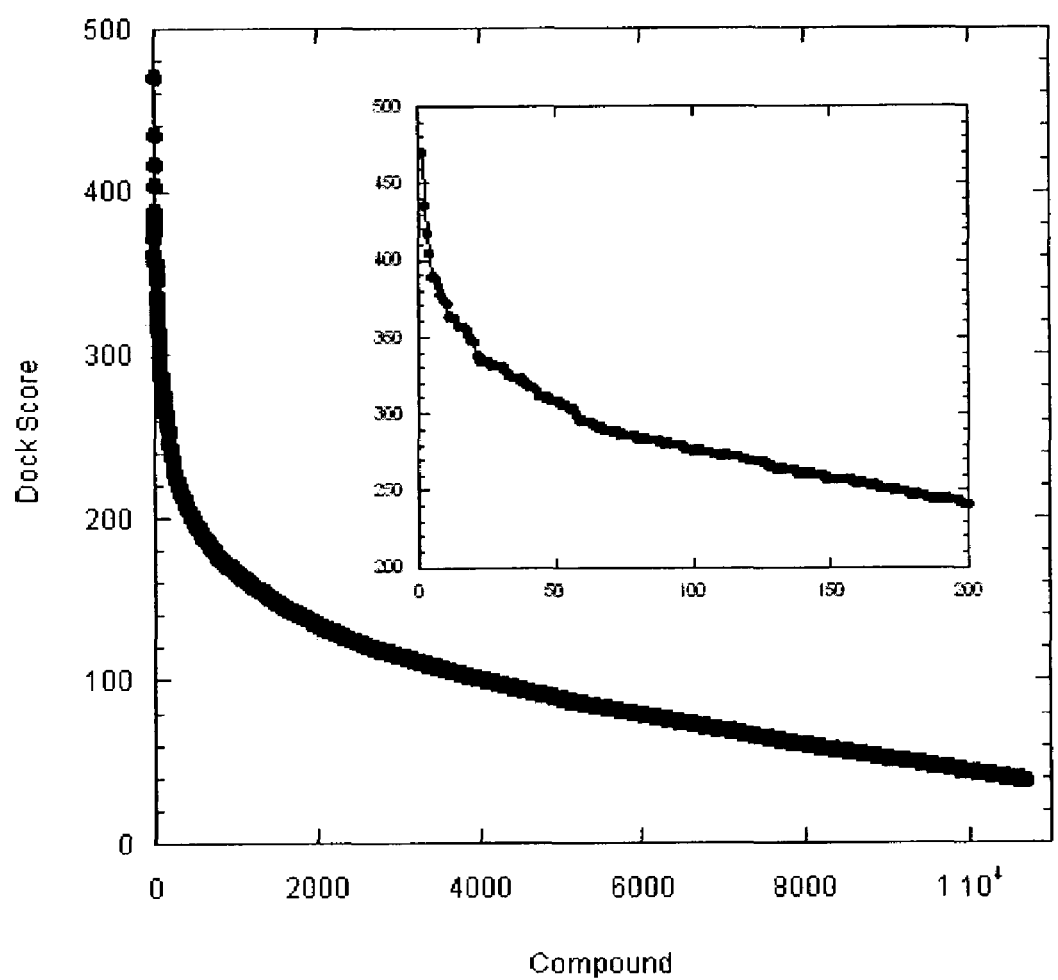
FIG. 1 graphically illustrates the dock score profile obtained for the top 10,000 compounds in the Available Chemicals Database (version 2000.1). The insert shows the dock score profile for the top 200 compounds.

This invention provides compositions and methods for modulating (increasing or decreasing) the secretion of mucus from mucosal surfaces of a mammal. The methods involve administering a composition comprising a compound or a peptide that can bind a $P2Y_2$ or $P2Y_1$ receptor. Examples of peptides of the invention include a peptide of any one of SEQ ID NO:44–47. A variety of compounds are provided herein that can also bind to a $P2Y_2$ or $P2Y_1$ receptor. The compositions and methods of the invention can change the quantity and quality of the secretions of the reproductive organs and influence the activity of a $P2Y_2$ or $P2Y_1$ receptor. For example, increased activation of $P2Y_2$ or $P2Y_1$ receptor results in increases in the secretion of mucin from the cell.

Mucins refer to a family of glycoproteins of high molecular weight, secreted or expressed by goblet and nongoblet epithelial cells of mucosal tissues. Mucins can form mucus, a highly hydrated gel of particular structure and function. Mucins from diverse species have similar structural features, particularly with regard to the mucin protein backbone. Nine distinct mucin genes have been identified (MUC 1, 2, 3, 4, MUC5AC, MUC5B, MUC6, 7 and 8). Mucins are glycoproteins containing from fifty to eighty percent carbohydrate. They are large, elongated molecules (molecular weight $10^5$ to $10^7$ daltons) with a protein backbone to which oligosaccharides are attached in a bottle-brush configuration. The oligosaccharide side chains, or bristles, can be highly variable in their make-up, indicating that the more basic functions of the molecule derive from the protein core. These molecules can be crosslinked through disulfide bridges to form very high molecular weight gels. Different tissues may produce different types of mucins.

According to the invention, the compounds and peptides provided herein can modulate (stimulate or decrease) mucin or mucus production. Influences on mucus secretion that may be provided by the invention include, but are not limited to, the quantity and type of mucin (e.g. sulfomucin and/or sialomucin), changes in viscosity, hydrogen ion retardation, hydrophobicity, changes in phospholipid content, glycosylation and sulfation, macromolecular assembly, surface tension, adhesivity, transport properties, elastic modulus, tensile properties, rigidity factors, recoil factors, spinnbarkeit, sperm penetration qualities, consistency, cellularity, ferning, and the like.

The compounds and methods of the invention can modulate the secretion of mucus from any mucosal surface in a mammal. For example, the mucosal surface can be a surface of a lung, a sinus, a nasal passage, an ear canal, an eye, a throat, or a reproductive canal (e.g. a female reproductive canal).

The compounds and methods of the invention can change the constitutive and stimulated secretions of the local reproductive system, including those of the vagina, cervix, uterus, fallopian tube, Bartholin or vestibular glands and urethral secretions. The methods and compositions of the invention can influence the function of the mucus genes found in the reproductive system, including, but not limited to genes that control mucus production in the cervix, uterus, and Bartholin's glands and other parts of the reproductive system with mucus secreting cells. The squamous epithelium of the lower genital tract (vagina; for example) and epithelial cells of the cervix can be treated by the methods of the invention. Included are methods to influence or change the secretary effects of the mucus genes, mucus secreting cells and cells that influence the properties of secretory and cell surface mucins of all the above mentioned glands of the reproductive system.

Mucus can be defined by its chemical, physical and biological properties. Rheological or flow properties of mucus include viscosity, rate of flow, shear index, spinnbarkeit or stretch of mucus due to increased viscoelasticity and ferning (crystallization) parameters. Changing or stimulating the hydration, viscosity, quantity or other properties of vaginal secretions can influence a variety of conditions and disorders, including, but not limited to contraception, infertility, menopause, dyspareunia, infections, and others related and unrelated conditions. Description of the function and anatomy of these organs can be found in Novak's Gynecology, 12$^{th}$ edition, eds. Berek, Adashi and Hillard, Williams and Wilkins, Baltimore, Md., 1996.

The invention therefore has at least two general utilities. First, the invention may increase the amount of mucus and/or the water content of secretions from mucosal surfaces. Second, the invention may be used to decrease the amount of mucus and/or inhibit the retention of mucus in organs that typically produce mucus.

The P2Y$_2$ Pathway

P2Y$_2$ receptors are P2-purinoceptors are transmembrane receptors on epithelial cells that interact with purines, particularly with ATP and UTP. P2-purinoceptors comprise two major families, P2X and P2Y. Each family consists of at least seven members (X$_{1-7}$ and Y$_{1-7}$). The P2X family represents cell membrane ligand-binding ion channels permeable to Na$^+$, K$^+$, and Ca$^{++}$. The P2Y-purinoceptors constitute G-protein-linked receptors, often coupled to phospholipase C and, hence, to inositol triphosphate formation. There are at least seven different subclasses of P2Y receptor, based upon agonist potency profiles. For a description of the various P2Y subtypes, see, for example, Abbrachio and Burnstock, Pharmac. Ther. 64, 445–475, 1994, the entire disclosure of which is incorporated herein by reference.

The P2Y$_2$ pathway can be manipulated by the methods of the invention. This pathway normally begins with the binding of nucleotide(s) or nucleoside(s) to the P2Y$_2$ receptor that is on or within the epithelial cell membrane. This pathway is typically linked to the activation of protein kinase C (PKC). Activation of protein kinase C leads to increased levels of inositol 1,4,5-triphosphate and diacylglycerol, resulting in the influx of Ca$^{2+}$ (Garrad et al., J. Biol. Chem. 1998, 273(45), 29437–29444). Protein kinase C activation has also been shown to affect mucin secretion (Li et al., J. Biol. Chem. 2001, 276(44):40982–90). Activated protein kinase C may phosphorylate a protein called myristoylated alanine-rich C kinase substrate (MARCKS) that then migrates from the plasma membrane into the cytoplasm of epithelial cells. The phosphorylated-MARCKS protein is dephosphorylated by protein phosphatase 2A (PP2A) in the cytoplasm, and thereby regains its capacity to bind membranes. MARCKS may associate with actin and myosin and may thereby mediate the movement of mucin-containing granules to the cell periphery. Hence, a series of biochemical events take place after dNTP-P2Y$_2$ receptor binding that eventually results in the secretion of mucin, a glycoprotein that is a component of mucus. Mucin causes a natural lubricating and moisturizing effect in the female genital tract.

According to the invention, the peptides and other compounds of the invention can activate the P2Y$_2$ receptor and thereby increase the production of mucus. Moreover, the peptides and other compounds of the invention can also modulate the activity of P2Y$_2$ receptor and thereby decrease the production or retention of mucus.

Peptides of the Invention

The peptides of the invention can bind to P2Y$_2$ or P2Y$_1$ receptors. Such peptides can activate or depress the activity of P2Y$_2$ or P2Y$_1$ receptors. Mixtures of peptides with different sequences are also contemplated for use in the compositions and methods of the invention. In general, the peptide sequences, peptide variants and mixtures of peptides are formulated and used in a manner that optimizes activation or inhibition of P2Y$_2$ or P2Y$_1$ receptors. Hence, the composition and formulations of the present peptides can be varied so that the desired secretion, viscosity and/or retention of mucus are achieved.

The size of a peptide agonist can vary. In general, a single amino acid may be too small to modulate mucus production. However, a peptide of about two amino acids may be large enough to provide optimal modulation of P2Y$_2$ or P2Y$_1$ receptors. Hence, peptides of about two or more amino acids are generally sufficiently long for P2Y$_2$ or P2Y$_1$ receptor modulation. While the overall length is not critical, peptides that are as long as or longer than about three amino acids are desirable. Other desirable peptides are longer than three amino acids.

There is no particular upper limit on peptide size. However, it is generally cheaper to make shorter peptides than longer peptides. Hence, the peptide agonists of the invention are generally shorter than about one hundred amino acids. Desirable peptide modulators are often shorter than about fifty amino acids.

The sequences of several representative peptide modulators of the invention are provided in Table 1.

TABLE 1

Examples of Peptide Modulators of P2Y$_2$ or P2Y$_1$ Receptors

| Sequence | SEQ ID |
|---|---|
| YARGDHWPFST | NO:1 |
| SVRGTRITCHDTSARELFSHFVAY | NO:2 |

TABLE 1-continued

Examples of Peptide Modulators of P2Y$_2$ or P2Y$_1$ Receptors

| Sequence | SEQ ID |
| --- | --- |
| LYYSFRSLDLSCHTLNAINMAYKITR | NO:3 |
| AAADLEPWNSTINCTWELDELCYKCRFNEDFKYVL | NO:4 |
| Ala-Ala-Ala-Ala-Glu | NO:5 |
| Ala-Gly-Ala-Ala | NO:6 |
| Ala-D-Ala-D-Ala-D-Ala-D-Ala-D-Ala | NO:7 |
| Gly-Gly-Ser-Ala | NO:8 |
| Gly-Gly-Gly | NO:9 |
| Gly-Gly-Gly-Ala | NO:10 |
| Gly-Gly-His-Gly | NO:11 |
| Gly-Ala-Ala-D-Ala-L-Ala | NO:12 |
| Gly-Gly-Ala-Gly | NO:13 |
| Gly-Ala-Ala | NO:14 |
| Ser-Glu-Gly | NO:15 |
| Gly-Gly-Glu-Ala | NO:16 |
| Glu-His-Gly | NO:17 |
| Gly-Ala-Asn | NO:18 |
| Ala-Ala-Ala-L-Pro | NO:19 |
| D-Ala-Ala-Ala-Ala | NO:20 |
| His-Gly-Gly | NO:21 |
| D-Glu-Glu | NO:22 |
| Gly-Gly-His-Ala | NO:23 |
| Lys-Gly-Glu | NO:24 |
| D-Glu-D-Glu | NO:25 |
| Gly-Pro-Ala | NO:26 |
| Ala-Ala-Tyr | NO:27 |
| Glu-Glu-Asp-OH | NO:28 |
| Gly-Gly-beta-Ala-Gly | NO:29 |
| Asp-Ala-Ser-Gly-Glu | NO:30 |
| Glu-Glu-Gln | NO:31 |
| Ala-Ala-Pro-Ala | NO:32 |
| Gly-Gly-Tyr-Ala | NO:33 |
| Trp-Gly-Gly-Tyr | NO:34 |

Each of the peptides listed in Table 1, as well as peptide having sequences like those in Formulae I–IV are useful as peptide modulators. Such peptides can have one or more amino acid substitutions, deletions, insertions or other modifications so long as the peptide variant can modulate mucus secretion or bind to a P2Y$_2$ or P2Y$_1$ receptor.

Amino acid residues of the isolated peptides can be genetically encoded L-amino acids, naturally occurring non-genetically encoded L-amino acids, synthetic L-amino acids or D-enantiomers of any of the above. The amino acid notations used herein for the twenty genetically encoded L-amino acids and common non-encoded amino acids are conventional and are as shown in Table 2.

TABLE 2

| Amino Acid | One-Letter Symbol | Common Abbreviation |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| 2,3-Diaminopropionic acid | | Dpr |
| a-Aminoisobutyric acid | | Aib |
| N-Methylglycine (sarcosine) | | MeGly |
| Ornithine | | Orn |
| Citrulline | | Cit |
| t-Butylalanine | | t-BuA |
| t-Butylglycine | | t-BuG |
| N-methylisoleucine | | MeIle |
| Phenylglycine | | Phg |
| Cyclohexylalanine | | Cha |
| Norleucine | | Nle |
| Naphthylalanine | | Nal |
| Pyridylalanine | | |
| 3-Benzothienyl alanine | | |
| 4-Chlorophenylalanine | | Phe(4-Cl) |
| 2-Fluorophenylalanine | | Phe(2-F) |
| 3-Fluorophenylalanine | | Phe(3-F) |
| 4-Fluorophenylalanine | | Phe(4-F) |
| Penicillamine | | Pen |
| 1,2,3,4-Tetrahydro-isoquinoline-3-carboxylic acid | | Tic |
| β-2-thienylalanine | | Thi |
| Methionine sulfoxide | | MSO |
| Homoarginine | | hArg |
| N-acetyl lysine | | AcLys |
| 2,4-Diamino butyric acid | | Dbu |
| ?-Aminophenylalanine | | Phe(pNH$_2$) |
| N-methylvaline | | MeVal |
| Homocysteine | | HCys |
| Homoserine | | HSer |
| ?-Amino hexanoic acid | | Aha |
| ?-Amino valeric acid | | Ava |
| 2,3-Diaminobutyric acid | | Dab |

Peptides that are encompassed within the scope of the invention can have one or more amino acids substituted with an amino acid of similar chemical and/or physical properties, so long as these variant peptides retain the ability to modulate mucus secretion or to bind one or more P2Y$_2$ or P2Y$_1$ receptors. Examples of modified peptides include those listed below in Table 3.

TABLE 3

Modified Peptides

| Sequence | SEQ ID: |
|---|---|
| Glycyl-L-alanyl-L-glutamine | NO: 35 |
| S-Nitrosoglutathione | NO: 36 |
| Glutathione-monoisopropyl-ester (reduced) | NO: 37 |
| L-Cystinyl-cystine | NO: 38 |
| Ac-His-His-Gly-His | NO: 39 |
| Gly-Ala-NH2 | NO: 40 |
| Ac-Glycyl-L-Glutamine | NO: 41 |
| Methoxycarbonyl-Phe-Gly | NO: 42 |
| 3-5-Diiodo-D-Tyr-Ala-Gly-Gly | NO: 43 |

Amino acids that are substitutable for each other generally reside within similar classes or subclasses. As is known to one of skill in the art, amino acids can be placed into three main classes: hydrophilic amino acids, hydrophobic amino acids and cysteine-like amino acids, depending primarily on the characteristics of the amino acid side chain. These main classes may be further divided into subclasses. Hydrophilic amino acids include amino acids having acidic, basic or polar side chains and hydrophobic amino acids include amino acids having aromatic or apolar side chains. Apolar amino acids may be further subdivided to include, among others, aliphatic amino acids. The definitions of the classes of amino acids as used herein are as follows:

"Hydrophobic Amino Acid" refers to an amino acid having a side chain that is uncharged at physiological pH and that is repelled by aqueous solution. Examples of genetically encoded hydrophobic amino acids include Ile, Leu and Val. Examples of non-genetically encoded hydrophobic amino acids include t-BuA.

"Aromatic Amino Acid" refers to a hydrophobic amino acid having a side chain containing at least one ring having a conjugated p-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Apolar Amino Acid" refers to a hydrophobic amino acid having a side chain that is generally uncharged at physiological pH and that is not polar. Examples of genetically encoded apolar amino acids include glycine, proline and methionine. Examples of non-encoded apolar amino acids include Cha.

"Aliphatic Amino Acid" refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Hydrophilic Amino Acid" refers to an amino acid having a side chain that is attracted by aqueous solution. Examples of genetically encoded hydrophilic amino acids include Ser and Lys. Examples of non-encoded hydrophilic amino acids include Cit and hCys.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminopropionic acid, 2,4-diaminobutyric acid and homoarginine.

"Polar Amino Acid" refers to a hydrophilic amino acid having a side chain that is uncharged at physiological pH, but which has a bond comprising a pair of electrons shared by two atoms where the electrons are held more closely by one of the atoms. Examples of genetically encoded polar amino acids include asparagine and glutamine. Examples of non-genetically encoded polar amino acids include citrulline, N-acetyl lysine and methionine sulfoxide.

"Cysteine-Like Amino Acid" refers to an amino acid having a side chain capable of forming a covalent linkage with a side chain of another amino acid residue, such as a disulfide linkage. Typically, cysteine-like amino acids generally have a side chain containing at least one thiol (SH) group. Examples of genetically encoded cysteine-like amino acids include cysteine. Examples of non-genetically encoded cysteine-like amino acids include homocysteine and penicillamine.

As will be appreciated by those having skill in the art, the above classifications are not absolute. Several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a peptide.

Certain commonly encountered amino acids that are not genetically encoded and that can be present, or substituted for an amino acid, in the peptides and peptide analogs and derivatives of the invention include, but are not limited to, β-alanine (b-Ala) and omega-amino acids such as 3-aminopropionic acid (Dap), 2,3-diaminopropionic acid (Dpr), 4-aminobutyric acid and so forth; a-aminoisobutyric acid (Aib); e-aminohexanoic acid (Aha); d-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe (pNH$_2$)); N-methyl valine (MeVal); homocysteine (hCys) and homoserine (hSer). These amino acids also fall into the categories defined above.

The classifications of the above-described genetically encoded and non-encoded amino acids are summarized in Table 4 below. It is to be understood that Table 4 is for illustrative purposes only and does not purport to be an exhaustive list of amino acid residues that may comprise the peptides and peptide analogues described herein. Other amino acid residues that are useful for making the peptides and peptide analogues described herein can be found, e.g., in Fasman, 1989, CRC Practical Handbook of Biochemistry and Molecular Biology, CRC Press, Inc., and the references cited therein. Amino acids not specifically mentioned herein can be conveniently classified into the above-described categories on the basis of known behavior and/or their characteristic chemical and/or physical properties as compared with amino acids specifically identified.

TABLE 4

| Classification | Genetically Encoded | Genetically Non-Encoded |
|---|---|---|
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-NH$_2$), DBU, A$_2$BU |
| Polar | Q, N, S, T, Y | Cit, AcLys, MSO, hSer |
| Cysteine-Like | C | Pen, hCys, β-methyl Cys |

Peptides of the invention can have any amino acid substituted by any similarly classified amino acid to create a variant peptide, so long as the peptide variant retains an ability to modulate mucus production or to bind one or more $P2Y_2$ or $P2Y_1$ receptors. Peptides of the invention can also have one or more amino acids replaced by a dissimilarly charged amino acid to generate a peptide derivative that has desirable properties in addition to binding one or more $P2Y_2$ or $P2Y_1$ receptors, for example, enhanced stability, enhanced mucus secretion or enhanced activation of $P2Y_2$ or $P2Y_1$ receptors.

A variety of peptides can therefore bind $P2Y_2$ or $P2Y_1$ receptors, including peptides having any one of SEQ ID NO:44–47.

SEQ ID NO:44, provided below, encompasses the following peptides.

$$Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}Xaa_{10}\text{-}Xaa_{11}$$

wherein $Xaa_1$ is an aromatic or polar amino acid;

$Xaa_2$ is an aliphatic amino acid;

$Xaa_3$, $Xaa_6$ are separately each a basic amino acid;

$Xaa_4$, $Xaa_8$ are separately each an apolar amino acid;

$Xaa_5$ is an acidic amino acid;

$Xaa_7$ and $Xaa_9$ are separately each an aromatic amino acid; and $Xaa_{10}$ and $Xaa_{11}$ are separately each a polar amino acid;

wherein the peptide is capable of binding to a $P2Y_2$ or $P2Y_1$ receptor. Such binding may increase $P2Y_2$ receptor activity and/or increase the production of mucus.

SEQ ID NO:45, provided below, is directed to peptides of the following structure.

$$Xaa_{12}\ Xaa_{13}\text{-}Xaa_{14}\text{-}Xaa_{15}\text{-}Xaa_{16}\text{-}Xaa_{17}\text{-}Xaa_{18}\text{-}Xaa_{19}\text{-}\\Xaa_{20}\text{-}Xaa_{21}\text{-}Xaa_{22}\text{-}Xaa_{23}\text{-}Xaa_{24}\text{-}Xaa_{25}\text{-}Xaa_{26}\text{-}\\Xaa_{27}\text{-}Xaa_{28}\text{-}Xaa_{29}\text{-}Xaa_{30}\text{-}Xaa_{31}\text{-}Xaa_{32}\text{-}Xaa_{33}\text{-}\\Xaa_{34}\text{-}Xaa_{35}$$

$Xaa_{12}$, $Xaa_{16}$, $Xaa_{19}$, $Xaa_{23}$, $Xaa_{24}$, and $Xaa_{30}$ are separately each a polar amino acid;

$Xaa_{13}$, $Xaa_{18}$, $Xaa_{25}$, $Xaa_{28}$, $Xaa_{33}$ and $Xaa_{34}$ are separately each an aliphatic amino acid;

$Xaa_{14}$, $Xaa_{17}$, $Xaa_{21}$, $Xaa_{26}$ and $Xaa_{31}$ are separately each a basic amino acid;

$Xaa_{15}$ is an apolar amino acid;

$Xaa_{20}$ is a cysteine-like amino acid;

$Xaa_{22}$ and $Xaa_{27}$ are separately each an acidic amino acid;

$Xaa_{29}$ and $Xaa_{32}$ are separately each an aromatic amino acid; and $Xaa_{35}$ is an aromatic or polar amino acid;

wherein the peptide is capable of binding to a $P2Y_2$ or $P2Y_1$ receptor. Such binding may increase $P2Y_2$ receptor activity and/or increase the production of mucus.

SEQ ID NO:46, provided below, is directed to peptides of the following structure.

$$Xaa_{36}\ Xaa_{37}\text{-}Xaa_{38}\text{-}Xaa_{39}\text{-}Xaa_{40}\text{-}Xaa_{41}\text{-}Xaa_{42}\text{-}Xaa_{43}\text{-}\\Xaa_{44}\text{-}Xaa_{45}\text{-}Xaa_{46}\text{-}Xaa_{47}\text{-}Xaa_{48}\text{-}Xaa_{49}\text{-}Xaa_{50}\text{-}\\Xaa_{51}\text{-}Xaa_{52}\text{-}Xaa_{53}\text{-}Xaa_{54}\text{-}Xaa_{55}\text{-}Xaa_{56}\text{-}Xaa_{57}\text{-}\\Xaa_{58}\text{-}Xaa_{59}\text{-}Xaa_{60}\text{-}Xaa_{61}$$

$Xaa_{36}$, $Xaa_{43}$, $Xaa_{45}$, $Xaa_{49}$, $Xaa_{50}$, $Xaa_{52}$, $Xaa_{53}$, $Xaa_{56}$ and $Xaa_{59}$ are separately each an aliphatic amino acid;

$Xaa_{37}$, $Xaa_{38}$, and $Xaa_{57}$ are separately each an aromatic or polar amino acid;

$Xaa_{39}$, $Xaa_{42}$, $Xaa_{46}$, $Xaa_{49}$, $Xaa_{51}$, $Xaa_{54}$ and $Xaa_{60}$ are separately each a polar amino acid;

$Xaa_{40}$ is an aromatic amino acid;

$Xaa_{41}$, $Xaa_{48}$, $Xaa_{58}$ and $Xaa_{61}$ are separately each a basic amino acid;

$Xaa_{44}$ is an acidic amino acid;

$Xaa_{47}$ is a cysteine-like amino acid; and $Xaa_{55}$ is an apolar amino acid;

wherein the peptide is capable of binding to a $P2Y_2$ or $P2Y_1$ receptor. Such binding may increase $P2Y_2$ receptor activity and/or increase the production of mucus.

SEQ ID NO:47, provided below, is directed to peptides of the following structure.

$$Xaa_{62}\ Xaa_{63}\text{-}Xaa_{64}\text{-}Xaa_{65}\text{-}Xaa_{66}\text{-}Xaa_{67}\text{-}Xaa_{68}\text{-}Xaa_{69}\text{-}\\Xaa_{70}\text{-}Xaa_{71}\text{-}Xaa_{72}\text{-}Xaa_{73}\text{-}Xaa_{74}\text{-}Xaa_{75}\text{-}Xaa_{76}\text{-}\\Xaa_{77}\text{-}Xaa_{78}\text{-}Xaa_{79}\text{-}Xaa_{80}\text{-}Xaa_{81}\text{-}Xaa_{82}\text{-}Xaa_{83}\text{-}\\Xaa_{84}\text{-}Xaa_{85}\text{-}Xaa_{86}\text{-}Xaa_{87}\text{-}Xaa_{88}\text{-}Xaa_{89}\text{-}Xaa_{90}\text{-}\\Xaa_{91}\text{-}Xaa_{92}\text{-}Xaa_{93}\text{-}Xaa_{94}\text{-}Xaa_{95}\text{-}Xaa_{96}$$

$Xaa_{62}$, $Xaa_{63}$, $Xaa_{64}$, $Xaa_{66}$, $Xaa_{73}$, $Xaa_{79}$, $Xaa_{82}$, $Xaa_{95}$ and $Xaa_{96}$ are separately each an aliphatic amino acid;

$Xaa_{65}$, $Xaa_{67}$, $Xaa_{78}$, $Xaa_{80}$, $Xaa_{81}$, $Xaa_{90}$ and $Xaa_{91}$ are separately each an acidic amino acid;

$Xaa_{68}$ is an apolar amino acid;

$Xaa_{69}$, $Xaa_{77}$, $Xaa_{88}$ and $Xaa_{92}$ are separately each an aromatic amino acid;

$Xaa_{70}$, $Xaa_{71}$, $Xaa_{72}$, $Xaa_{74}$, $Xaa_{76}$ and $Xaa_{89}$ are separately each a polar amino acid;

$Xaa_{75}$, $Xaa_{83}$ and $Xaa_{86}$ are a cysteine-like amino acid;

$Xaa_{84}$ and $Xaa_{94}$ are separately each an aromatic or polar amino acid;

$Xaa_{85}$, $Xaa_{87}$ and $Xaa_{93}$ are separately each a basic amino acid;

wherein the peptide is capable of binding to a $P2Y_2$ or $P2Y_1$ receptor. Such binding may increase $P2Y_2$ receptor activity and/or increase the production of mucus.

Compounds that can Bind to $P2y_2$ Receptors

Compounds that can bind to $P2Y_2$ or $P2Y_1$ receptors are of the appropriate size and hydrophobicity or charge distribution to optimally occupy a $P2Y_2$ or $P2Y_1$ receptor site. To ascertain whether a compound can bind to a P2Y$_2$ or P2Y$_1$ receptor site, the coordinates, hydrophobicity and charge of atoms within a P2Y$_2$ or P2Y$_1$ receptor site can be mapped and computer searches can be performed to ascertain whether a test compound can appropriately interact or bind within a site of that size, hydrophobicity or charge. For example, test compounds can be screened for binding to a P2Y$_2$ or P2Y$_1$ receptor site using the program suite LigandFit from MSI, Inc. Crystal structures of a P2Y$_2$ or P2Y$_1$ receptor site that are available to one of skill in the art can be used as a source of protein atomic coordinates for a P2Y$_2$ or P2Y$_1$ receptor site. In one such search yielded about two hundred compounds, when using the chick P2Y$_1$ purinoceptor complexed with adenosine triphosphate (PDB code 1DDD) as the source of protein atomic coordinates.

Examples of compounds that can bind to a P2Y$_2$ or P2Y$_1$ receptor include p-nitrobenzyloxycarbonyloxysuccinimide; 1-benzyl-2-2-5-dioxotetrahydro-1H-pyrrol-1-yl-pyrrolidine-1-2-dicarboxylate; 5-(3-methoxycarbonylacryloyl) isophthalic acid dimethyl ester; 6-O-β-glucopyranosyl-β-D-glucose; cyclobutane-1-2-3-4-tetracarboxylic acid dimethyl ester; mono-2-acryloyloxyethyl-succinate; 2-benzyloxycarbonylamino-3-methylbutyric acid, 2-5-dioxo-pyrrolidin-1-yl-ester; tris(trichlorosilylethyl)methylsilane; 2-5-dioxotetrahydro-1H-pyrrol-1-yl-2-benzyloxycarbonylamino-3-phenylpropane; 2-chloroethylcarbamic acid, 2-5-dioxo-pyrrolidin-1-yl ester; mono-2-methacryloyloxyethyl-succinate; galactosyl dialyceride; 3-beta-hydroxy-5-alpha-androstan-17-one-beta-D-glucoside; N-4-5-dimethoxy-2-nitrobenzyloxycarbonyl-L-tryptophan; 2-amino-2-4-chlorobenzoyloxyiminoethyl-piyalate; disuccinimidyl sebacate; 2-2-2-trichloro-1-2-methoxy-phenylamino-ethyl-carbamic-acid-benzyl-ester; 2-acetamido-2-deoxy-6-O-beta-D-galactopyranosyl-D-galactopyranose; 2-benzyloxycarbonylamino-3-hydroxy-propionylaminoacetic acid ethyl ester; 2-benzyloxycarbonylmethylsulfanyl-6-hydroxy-pyrimidine-4-carboxylic-acid-methyl-ester; 3-(2-2-2-trichloro-1-isobutyrylamino)ethylthioureidobenzoic acid; ester of 2-diazo-1-naphthol-5-sulphone with 2-3-4-trihydroxybenzophenone; 4-5 dihydroxy-6-hydroxymethyl-2-methoxy-4H-pyran-3-yl-carbamic acid benzyl ester; diethyl-trans-1-2-cyclopropanedicarboxylate; 2-allyloxycarbonylmethylsulfanyl-6-hydroxy-pyrimidine-4-carboxylic acid methyl ester; 1-O-alpha-D-glucopyranosyl-D-fructose; methyl-2-2-4-chlorophenylsulfonylamino-acetylamino-2-phenylacetate; N-(2-hydroxy-4-oxo-4-phenylbut-2-enoyl)-2-methylquinoline-4-carbohydrazide; or DL-Djenkolic-acid (also called L-5, 5'-Methylenebis (cysteine) L-Djenkolic acid, CAS 498-59-9).

Methods of Use

The present invention is directed to a variety of methods of treating or preventing dryness or mucosal build-up in organs having mucosal surfaces. The peptides and compounds of the present invention can bind P2Y$_2$ and/or P2Y$_1$ purinergic receptors. These compounds and peptides are useful in the treatment of mammals including humans suffering from chronic obstructive pulmonary diseases such as chronic bronchitis, Primary Ciliary Dyskinesia, cystic fibrosis, as well as prevention of pneumonia. Furthermore, because of their general ability to clear retained mucus secretions, the compounds of the present invention are also useful in the treatment of sinusitis, otitis media and nasolacrimal duct obstruction in mammals. Additionally, the compounds of the present invention are useful for treating mammals with dry eye, vaginal and/or reproductive problems in a female mammal, vaginal dryness and retinal detachment.

Though the compounds of the present invention are primarily concerned with the treatment of human subjects, they may also be employed for the treatment of other mammalian subjects such as dogs and cats for veterinary purposes. Hence, the term "mammal," as used herein, refers to an animal, in general, a warm-blooded animal. Mammals include cattle, buffalo, sheep, goats, pigs, horses, dogs, cats, rats, rabbits, mice, and humans. Also included are other livestock, domesticated animals and captive animals.

These methods involve administering to a mammal an effective amount of a compound or peptide agonist that can modulate mucus secretion or that can bind to a P2Y$_2$ or P2Y$_1$ receptor.

Treatment of, or treating, a mammal is intended to include modulation of mucus levels to enhance or diminish mucus production in the mammal. In some embodiments, such treatment involves alleviating or diminishing the symptoms of cystic fibrosis, pneumonia, vaginal dryness, or chronic obstructive pulmonary diseases such as chronic bronchitis or Primary Ciliary Dyskinesia in a mammal. The treatment therefore can include alleviation or diminishment of more than one problem associated with mucus secretion in a mammal.

In one embodiment, the method increases secretion of mucus in vaginal or cervical epithelial cells. In another embodiment, the method involves activating P2Y$_2$ or P2Y$_1$ receptors in vaginal or cervical cells. Such methods can prevent or treat vaginal dryness in a mammal, or maintain or enhance the normal protective function of vaginal mucus in a mammal.

Treatment involves administering an effective amount of a compound or peptide of the invention to a mammal. The peptides and/or compounds may be administered as a composition that contains other ingredients.

Female Reproductive System

As an active gatekeeper to the internal reproductive organs, the uterine cervix plays a critical role in reproduction. The following functions can be attributed to vaginal/cervical mucus and its role in reproduction: 1) Semen is filtered at the cervical os and sperm allowed entry into the uterus from a relatively hostile vaginal environment; 2) Sperm are nurtured within the cervical canal and supported and prepared for capacitation; 3) Sperm are stored and later released in order to co-ordinate with ovulation. Katz, D. F. Human Cervical Mucous: Research Update. Am. J. Obstet. Gynecol. 1991:165:1984–6.

Under the influence of estrogen, cervical mucus becomes thin and less viscous, with a ferning pattern seen when spread on a slide. Katz, D. F. Human Cervical Mucous: Research Update. Am. J. Obstet. Gynecol. 1991:165:1984–6. The actual mechanism whereby estrogen changes the cervical mucus is not clearly understood. But see, Nicosia S V. Physiology of the Cervical Mucus. Sem. In Reproductive Endocrinology. 1986;4:313–321. Cervical mucus is a mixture of mucin secreted by the mucus cells and transudation of capillary exudates, which include water (85–98%), electrolytes, serum and locally derived proteins. The mucins are responsible for the Theological properties of mucus, but comprise less than 1% in volume. Apparently, during the mid-cycle, estrogens stimulate the stromal cells, which in turn stimulate the mucus cells. The mucus produced during this time has a higher water content, which accounts for part of the Theological changes such as ferning.

Under the influence of estrogen, the human cervix secretes a profuse, clear and thin mucus, at a rate of about 600 mg of mucus a day, in the pre-ovulatory and ovulatory phases of the menstrual cycle. Under the influence of progestins, this rate decreases to 20–60 mg/day and the mucus is thick and viscous. Moghissi, K S. The function of the cervix infertility. Fert. Steril. 1972 23:295–306.

The viscosity of cervical mucus changes in a parallel fashion with externally administered progestins given as contraceptive products. For example, Norplant, a levo-norgestrel containing implant, changes cervical mucus within three days of insertion and this action is considered one of the critical factors responsible for its contraceptive action. Dunson T R et al. Timing on onset of contraceptive effectiveness in Norplant implant users. Part I. Changes in cervical mucus. Fert. Steril. 1998:69:258–66. A similar finding was shown with another progestin only product—Depo-Provera. Petta C A et al. Timing of onset of contraceptive effectiveness in Depo-Provera users: Part I. Changes in cervical mucus. Fertil Steril. 1998:69:252–7. Clearly, changes in cervical mucus could have a contraceptive effect because the secretion of progesterone is associated with a considerable decrease in fecundity and a closing of the window of fertility.

Compositions

The compositions of the invention are administered to improve the health of mucosal surfaces, to stimulate secretion of lubricating fluids and/or to reduce retention of viscous fluids in organs that normally have mucosal surfaces. A composition of the invention comprises an effective amount of a compound or peptide of the invention and a pharmaceutically acceptable carrier. Mixtures of compounds and/or peptides can also be administered.

To achieve the desired effect(s), the composition may be administered as single or divided dosages, for example, of at least about 0.001 µg to about 100 to 200 mg peptide or compound per kilogram of body weight, of about 0.01 µg to about 30 to 50 mg peptide or compound per kilogram of body weight, about 1.0 µg to about 10 to 20 mg peptide or compound per kilogram of body weight or about 10 µg to about 1.0 to about 10 mg peptide or compound per kilogram of body weight, although other dosages may provide beneficial results. The amount administered will vary depending on various factors including, but not limited to, the disease, the weight, the physical condition, the health, the age of the mammal, and whether prevention of reproduction or treatment of vaginal dryness is to be achieved. Such factors can be readily determined by the clinician employing animal models or other test systems that are available in the art.

Administration of the therapeutic agents in accordance with the present invention may be in a single dose, in multiple doses, in a continuous or intermittent manner, depending, for example, upon the recipient's physiological condition, whether the purpose of the administration is therapeutic or prophylactic, and other factors known to skilled practitioners. The administration of the compositions of the invention may be essentially continuous over a pre-selected period of time or may be in a series of spaced doses. Local administration is generally contemplated.

The compositions are prepared by combining the active ingredients in the appropriate concentrations. Other active or inactive agents selected by one of skill in the art can optionally be added. The absolute weight of a given active agent included in a unit dose can vary widely. For example, about 0.001 µg to about 50 mg, or about 0.01 µg to about 10 mg, or about 0.1 µg to about 1 mg, of at least one peptide or compound of the invention can be administered. Alternatively, the unit dosage can vary from about 0.001 µg to about 1000 µg, from about 0.01 µg to about 750 µg, from about 0.1 µg to about 1 mg, from about 1.0 µg to about 750 µg, from about 2.5 µg to about 600 µg, from about 5.0 µg to about 500 µg, or from about 7.5 µg to about 400 µg of at least one peptide or compound of the invention.

Daily doses of the compositions of the invention can vary as well. Such daily doses can range, for example, from about 0.001 mg/day to about 50 mg/day, from about 0.01 mg/day to about 25 mg/day, from about 0.1 mg/day to about 12 mg/day, from about 0.1 mg/day to about 8 mg/day, from about 0.1 mg/day to about 4 mg/day, and from about 0.1 mg/day to about 2 mg/day of at least one peptide or compound of the invention.

Thus, one or more suitable unit dosage forms comprising the therapeutic compositions of the invention can be administered by a variety of routes including oral, parenteral (including subcutaneous, intravenous, intramuscular and intraperitoneal), rectal, dermal, transdermal, intrathoracic, intrapulmonary intravaginal and intranasal (respiratory) routes. The therapeutic compositions may also be formulated for sustained release (for example, using microencapsulation, see WO 94/07529, and U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

When the therapeutic compositions of the invention are prepared for intravaginal administration, they are generally combined with a pharmaceutically acceptable carrier, diluent or excipient to form a pharmaceutical formulation, or unit dosage form. For intravaginal administration, the compositions may be present as a solution, a suspension, an emulsion, a powder, a granular formulation, or in a natural or synthetic polymer or resin. The active compositions may also be presented as a bolus or paste. Intravaginally administered peptides or compounds of the invention can also be formulated for sustained release, e.g., the peptides or compounds can be coated, micro-encapsulated, or otherwise placed within a sustained delivery device. The total active ingredients in such formulations comprise from 0.1 to 99.9% by weight of the formulation.

The term "pharmaceutically acceptable" means a carrier, diluent, excipient, and/or salt is compatible with the other ingredients of the formulation, and not deleterious to the recipient thereof.

Pharmaceutical formulations containing the therapeutic compositions of the invention can be prepared by procedures known in the art using well-known and readily available ingredients. For example, the composition can be formulated with common excipients, diluents, or carriers, and formed into tablets, capsules, lotions, solutions, suspensions, powders, aerosols, creams and the like. Examples of excipients, diluents, and carriers that are suitable for such fonnulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface-active agents such as cetyl alcohol and glycerol monostearate can be included. Adsorptive carriers such as kaolin and bentonite can be added. Lubricants such as talc, calcium and magnesium stearate, and solid polyethyl glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

The therapeutic compositions of the invention can also be formulated as emulsions, suspensions, aqueous or anhydrous solutions or dispersions, or alternatively the form of an emulsion or suspension or salve for convenient intravaginal administration. The active compositions and other ingredients may form suspensions, solutions, or emulsions in oily or aqueous vehicles, and may contain formulatory agents such as suspending, stabilizing and/or dispersing agents. Alternatively, the active compositions and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$–$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

It is possible to add, if necessary, an adjuvant chosen from antioxidants, surfactants, other preservatives, film forming, keratolytic or comedolytic agents, perfumes, flavorings and colorings. Antioxidants such as t-butylhydroquinone, butylated hydroxyanisole, butylated hydroxytoluene and a-tocopherol and its derivatives can also be added.

Additionally, the compositions are well suited to formulation as sustained release dosage forms and the like. The formulations can be so constituted that they release the peptides and other active ingredients within or onto a mucosal surface over a period of time. Coatings, envelopes, and protective matrices may be made, for example, from polymeric substances, such as polylactide-glycolates, liposomes, microemulsions, microparticles, nanoparticles, or waxes.

For intravaginal administration, the therapeutic agents may be formulated as is known in the art for direct application to the vaginal area. Forms chiefly conditioned for vaginal application take the form, for example, of milks, gels, dispersions, microemulsions, lotions thickened to a greater or lesser extent, impregnated pads, ointments, aerosol formulations (e.g., sprays or foams), creams, pastes, jellies, sprays, and aerosols. Alternatively, the composition can be formulated to be part of an adhesive polymer, such as polyacrylate or acrylate/vinyl acetate copolymer.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays are conveniently delivered from pressurized packs, for example, via a specially shaped container or applicator. The active compositions can also be delivered via iontophoresis, e.g., as disclosed in U.S. Pat. Nos. 4,140,122; 4,383,529; or 4,051,842. The percent by weight of a therapeutic agent of the invention present in a formulation will depend on various factors, but generally will be from 0.01% to 95% of the total weight of the formulation, and typically 0.1–85% by weight.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0–8.0.

Furthermore, the active ingredients may also be used in combination with other therapeutic agents, for example, anti-microbial agents, anti-fungal agents, anti-yeast agents and the like, whether for the conditions described or some other condition.

The present invention further pertains to a packaged composition for controlling reproduction and/or vaginal dryness that is provided in a kit or other container. The kit or container holds a therapeutically effective amount of the composition for controlling reproduction and/or vaginal dryness and instructions for using the composition for promoting reproductive health, controlling reproduction and/or preventing vaginal dryness. The composition includes a compound or peptide of the present invention, in a therapeutically effective amount such that reproductive health, vaginal dryness or reproduction is controlled.

The following examples are intended to further illustrate certain aspects of the invention but are not intended to be limiting thereof.

EXAMPLE 1

Identification of $P2Y_2$ or $P2Y_1$ Receptor Ligands

Automated molecular docking. The crystal structure of chick P2Y1 purinoceptor complexed with adenosine triphosphate (PDB code 1DDD) was the source of protein atomic coordinates. Prior to docking computations, the coordinate file was edited to remove all water molecules and the inhibitor. Docking was carried out using the program suite LigandFit from MSI, Inc. A search grid of 35×35×35 A was constructed in the region where the ATP molecule was found. Grid points were separated by 0.2 A. All rotatable dihedrals of the small molecule library (300,000 compounds in the Available Chemicals Database version 2000.1) were allowed to move freely and the molecules were docked via a Monte Carlo configuration search. The docking run was conducted with full electrostatics. For each molecule the docking run was allowed to save up to 1000 possible solutions, which were then automatically clustered into groups. A group was defined by a root mean squared (rms) deviation of less than or equal to 0.3 A. The clusters were then scored based on the calculated intermolecular energy of the solution. A single top solution was saved to disk. The top 10,000 scoring unique compounds were redocked into the grid area using a combined quantum mechanical, molecular mechanics routine that allowed movement of amino acid side chains that were within 3 Å of the ligand. The final scoring function is shown in FIG. 1.

The top 200 compounds were further analyzed. Novel P2Y2 purinoceptor binding compounds are presented in Tables 5, 6 and 7 along with their respective dock scores (higher numbers are better). Three classes of compounds were identified: peptides, modified peptides, and small organic molecules.

TABLE 5

High scoring peptide P2Y$_2$ receptor binding agents.

| | |
|---|---|
| 469.90 | Ala-Ala-Ala-Ala-Glu |
| 435.58 | Ala-Gly-Ala-Ala |
| 404.15 | Ala-D-Ala-D-Ala-D-Ala-D-Ala-D-Ala |
| 388.85 | Gly-Gly-Ser-Ala |
| 387.59 | Gly-Gly-Gly |
| 377.31 | Gly-Gly-Gly-Ala |
| 356.19 | Gly-Gly-His-Gly |
| 350.80 | Gly-Ala-Ala-D-Ala-L-Ala |
| 346.42 | Gly-Gly-Ala-Gly |
| 337.57 | Gly-Ala-Ala |
| 335.16 | Ser-Glu-Gly |
| 334.61 | Gly-Gly-Glu-Ala |
| 334.25 | Glu-His-Gly |
| 322.22 | Gly-Ala-Asn |
| 321.67 | Ala-Ala-Ala-L-Pro |
| 319.96 | D-Ala-Ala-Ala-Ala |
| 318.61 | His-Gly-Gly |
| 316.89 | D-Glu-Glu |
| 316.24 | Gly-Gly-His-Ala |
| 310.20 | Lys-Gly-Glu |
| 310.17 | D-Glu-D-Glu |
| 309.56 | Gly-Pro-Ala |
| 307.96 | Ala-Ala-Tyr |
| 295.31 | Glu-Glu-Asp-OH |
| 294.34 | Gly-Gly-beta-Ala-Gly |
| 294.05 | Asp-Ala-Ser-Gly-Glu |
| 291.13 | Glu-Glu-Gln |
| 290.16 | Ala-Ala-Pro-Ala |
| 285.22 | Gly-Gly-Tyr-Ala |
| 277.15 | Trp-Gly-Gly-Tyr |

Where all amino acids are in the L configuration unless denoted by a 'D'

TABLE 6

High scoring modified peptide-based P2Y$_2$ receptor binding agents.

| | |
|---|---|
| 330.41 | Glycyl-1-alanyl-1-glutamine |
| 328.74 | S-nitrosoglutathione |
| 322.64 | Glutathione-monoisopropyl-ester (reduced) |
| 304.85 | L-cystinyl-cystine |
| 290.92 | Ac-His-His-Gly-His |
| 289.21 | Gly-Ala-NH2 |
| 286.07 | Ac-Glycyl-L-Glutamine |
| 272.55 | Methoxycarbonyl-Phe-Gly |
| 261.04 | 3-5-Diiodo-D-Tyr-Ala-Gly-Gly |

Where Ac = acetylated N-terminus, NH2 is an amidated C-terminus

TABLE 7

High scoring small molecule P2Y$_2$ receptor binding agents.

| | |
|---|---|
| 298.94 | P-nitrobenzyl-oxycarbonyloxy-succinimide |
| 287.52 | 1-benzyl-2-2-5-dioxotetrahydro-1H-pyrrol-1-yl-pyrrolidine-1-2-dicarboxylate |
| 283.81 | 5-3-methoxycarbonyl-acryloyl-isophthalic-acid-dimethyl-ester |
| 283.14 | Gentiobiose |
| 280.22 | Cyclobutane-1-2-3-4-tetracarboxylic-acid-dimethyl-ester |
| 279.52 | Mono-2-acryloyloxyethyl-succinate |
| 279.27 | 2-benzyloxycarbonylamino-3-methyl-butyric-acid-2-5-dioxo-pyrrolidin-1-yl-ester |
| 279.24 | Tris trichlorosilylethylmethylsilane |
| 275.24 | 2-5-dioxotetrahydro-1H-pyrrol-1-yl-2-benzyloxycarbonylamino-3-phenylpropan |
| 274.86 | 2-chloro-ethyl-carbamic-acid-2-5-dioxo-pyrrolidin-1-yl-ester |
| 274.49 | Mono-2-methacryloyloxyethyl-succinate |
| 261.23 | Galactosyl-diglyceride |
| 257.37 | 3-beta-hydroxy-5-alpha-androstan-17-one-beta-D-glucoside |
| 257.34 | N-4-5-dimethoxy-2-nitrobenzyloxycarbonyl-L-tryptophan |
| 255.96 | 2-amino-2-4-chlorobenzoyloxyiminoethyl-pivalate |
| 250.34 | Disuccinimidyl-sebacate |
| 249.60 | 2-2-2-trichloro-1-2-methoxy-phenylamino-ethyl-carbamic-acid-benzyl-ester |
| 248.56 | 2-acetamido-2-deoxy-6-O-beta-D-galactopyranosyl-D-galactopyranose |
| 247.48 | 2-benzyloxycarbonylamino-3-hydroxy-propionylamino-acetic-acid-ethyl-ester |
| 232.18 | 2-benzyloxycarbonylmethylsulfanyl-6-ho-pyrimidine-4-carboxylic-acid-methyl-ester |
| 231.82 | 3-3-2-2-2-trichloro-1-isobutyrylamino-ethyl-thioureido-benzoic-acid |
| 231.67 | Ester-of-2-diazo-1-naphthol-5-sulphone-with-2-3-4-trihydroxybenzophenone |
| 231.54 | 4-5-dihydroxy-6-hydroxymethyl-2-meo-4h-pyran-3-yl-carbamic-acid-benzyl-ester |
| 228.17 | Diethyl-trans-1-2-cyclopropanedicarboxylate |
| 227.97 | 2-allyloxycarbonylmethylsulfanyl-6-HO-pyrimidine-4-carboxylic-acid-methyl-ester |
| 219.17 | 1-O-alpha-D-glucopyranosyl-D-fructose |
| 213.32 | Methyl-2-2-4-chlorophenylsulfonylaminoacetylamino-2-phenylacetate |
| 211.61 | N + 4-2-hydroxy-4-oxo-4-phenylbut-2-enoyl-2-methylquinoline-4-carbohydrazide |
| 205.54 | DL-Djenkolic-acid |

All publications and patents are incorporated by reference herein, as though individually incorporated by reference. The invention is not limited to the exact details shown and described, for it should be understood that many variations and modifications may be made while remaining within the spirit and scope of the invention defined by the statements.

What is claimed:

1. A method for modulating the activity of a $P2Y_2$ or $P2Y_1$ receptor in a mucosal surface of a mammal comprising administering to the mammal in need thereof a composition comprising a daily effective dose of about 0.001 mg to about 50 mg of a compound that can bind a $P2Y_2$ or $P2Y_1$ receptor and a pharmaceutically acceptable excipient, wherein the compound comprises any one of p-nitrobenzyloxycarbonyloxysuccinimide; 1-benzyl-2-2-5-dioxotetrahydro-1H-pyrrol-1-yl-pyrrolidine-1-2-dicarboxylate; 5-(3-methoxycarbonylacryloyl)isophthalic acid dimethyl ester; 6-O-β-glucopyranosyl-β-D-glucose; cyclobutane-1-2-3-4-tetracarboxylic acid dimethyl ester; mono-2-acryloyloxyethyl-succinate; 2-benzyloxycarbonylamino-3-methylbutyric acid, 2-5-dioxo-pyrrolidin-1-yl-ester; tris(trichlorosilylethyl)methylsilane; 2-5-dioxotetrahydro-1H-pyrrol-1-yl-2-benzyloxycarbonylamino-3-phenylpropane 2-chloroethylcarbamic acid, 2-5-dioxo-pyrrolidin-1-yl ester; mono-2-methacryloyloxyethyl-succinate; 3-beta-hydroxy-5-alpha-androstan-17-one-beta-D-glucoside; N-4-5-dimethoxy-2-nitrobenzyloxycarbonyl-L-tryptophan; 2-amino-2-4-chlorobenzoyloxyiminoethyl-pivalate; disuccinimidyl sebacate; 2-2-2-trichloro-1-2-methoxy-phenylamino-ethyl-carbamic-acid-benzyl-ester; 2-acetamido-2-deoxy-6-O-beta-D-galactopyranosyl-D-galactopyranose; 2-benzyloxycarbonylamino-3-hydroxy-propionylaminoacetic acid ethyl ester; 2-benzyloxycarbonylmethylsulfanyl-6-hydroxy-pyrimidine-4-carboxylic-acid-methyl-ester-3-(2-2-2-trichloro-1-isobutyrylamino)ethylthioureidobenzoic acid; ester of 2-diazo-1-naphthol-5-sulphone with 2-3-4-trihydroxybenzophenone; 4-5-dihydroxy-6-hydroxymethyl-2-methoxy-4H-pyran-3-yl-carbamic acid benzyl ester; diethyl-trans-1-2-cyclopropanedicarboxylate; 2-allyloxycarbonylmethylsulfanyl-6-hydroxy-pyrimidine-4-carboxylic acid methyl ester; 1-O-alpha-D-glucopyranosyl-D-fructose; methyl-2-2-4-chlorophenylsulfonylamino-acetylamino-2-phenylacetate; N-(2-hydroxy-4-oxo-4-phenylbut-2-enoyl)-2-methylquinoline-4-carbohydrazide; or DL-Djenkolic-acid, with the proviso that when the compound is 6-O-β-glucopyranosyl-β-D-glucose or DL-Djenkolic-acid, said composition is not administered dermally or transdermally.

2. A method of preventing or treating vaginal dryness in a mammal in need of such prevention or treatment comprising administering to the vaginal cavity an effective amount of a composition comprising a compound that can bind a $P2Y_2$ or $P2Y_1$ receptor and a pharmaceutically acceptable excipient for use in the vaginal cavity area, wherein the compound comprises any one of p-nitrobenzyloxycarbonyloxysuccinimide; 1-benzyl-2-2-5-dioxotetrahydro-1H-pyrrol-1-yl-pyrrolidine-1-2-dicarboxylate;-5-(3-methoxycarbonylacryloyl)isophthalic acid dimethyl ester; 6-O-β-glucopyranosyl-β-D-glucose; cyclobutane-1-2-3-4-tetracarboxylic acid dimethyl ester; mono-2-acryloyloxyethyl-succinate; 2-benzyloxycarbonylamino-3-methylbutyric acid, 2-5-dioxo-pyrrolidin-1-yl-ester; tris(trichlorosilylethyl)methylsilane; 2-5-dioxotetrahydro-1H-pyrrol-1-yl-2-benzyloxycarbonylamino-3-phenylpropane-2-chloroethylcarbamic acid, 2-5-dioxo-pyrrolidin-1-yl ester; mono-2-methacryloyloxyethyl-succinate; galactosyl diglyceride; 3-beta-hydroxy-5-alpha-androstan-17-one-beta-D-glucoside; N-4-5-dimethoxy-2-nitrobenzyloxycarbonyl-L-tryptophan; 2-amino-2-4-chlorobenzoyloxyiminoethyl-pivalate; disuccinimidyl sebacate; 2-2-2-trichloro-1-2-methoxy-phenylamino-ethyl-carbamic-acid-benzyl-ester; 2-acetamido-2-deoxy-6-O-beta-D-galactopyranosyl-D-galactopyranose; 2-benzyloxycarbonylamino-3-hydroxy-propionylaminoacetic acid ethyl ester; 2-benzyloxycarbonylmethylsulfanyl-6-hydroxy-pyrimidine-4-carboxylic-acid-methyl-ester; 3-(2-2-2-trichloro-1-isobutyrylamino)ethylthioureidobenzoic acid; ester of 2-diazo-1-naphthol-5-sulphone with 2-3-4-trihydroxybenzophenone; 4-5-dihydroxy-6-hydroxymethyl-2-methoxy-4H-pyran-3-yl-carbamic acid benzyl ester; diethyl-trans-1-2-cyclopropanedicarboxylate; 2-allyloxycarbonylmethylsulfanyl-6-hydroxy-pyrimidine-4-carboxylic acid methyl ester; 1-O-alpha-D-glucopyranosyl-D-fructose; methyl-2-2-4-chlorophenylsulfonylamino-acetylamino-2-phenylacetate; N-(2-hydroxy-4-oxo-4-phenylbut-2-enoyl)-2-methylquinoline-4-carbohydrazide; or DL-Dj enkolic-acid.

3. The method of claim 2, wherein the composition comprises a lotion, cream, gel, spray, foam or vaginal insert.

4. A method of treating cystic fibrosis in a mammal comprising administering to the mammal an effective amount of a composition comprising a compound that can bind a $P2Y_2$ or $P2Y_1$ receptor and a pharmaceutically acceptable excipient, wherein the compound comprises any one of p-nitrobenzyloxycarbonyl-oxysuccinimide; 1-benzyl-2-2-5-dioxotetrahydro-1H-pyrrol-1-yl-pyrrolidine-1-2-dicarboxylate; 5-(3-methoxycarbonylacryloyl)isophthalic acid dimethyl ester; 6-O-β-glucopyranosyl-β-D-glucose; cyclobutane-1-2-3-4-tetracarboxylic acid dimethyl ester; mono-2-acryloyloxyethyl-succinate; 2-benzyloxycarbonylamino-3-methylbutyric acid, 2-5-dioxo-pyrrolidin-1-yl-ester; tris(trichlorosilylethyl)methylsilane; 2-5-dioxotetrahydro-1H-pyrrol-1-yl-2-benzyloxycarbonylamino-3-phenylpropane; 2-chloroethylcarbamic acid, 2-5-dioxo-pyrrolidin-1-yl ester; mono-2-methacryloyloxyethyl-succinate; galactosyl diglyceride; 3-beta-hydroxy-5-alpha-androstan-17-one-beta-D-glucoside; N-4-5-dimethoxy-2-nitrobenzyloxycarbonyl-L-tryptophan; 2-amino-2-4-chlorobenzoyloxyiminoethyl-piyalate; disuccinimidyl sebacate; 2-2-2-trichloro-1-2-methoxy-phenylamino-ethyl-carbamic-acid-benzyl-ester; 2-acetamido-2-deoxy-6-O-beta-D-galactopyranosyl-D-galactopyranose; 2-benzyloxycarbonylamino-3-hydroxy-propionylaminoacetic acid ethyl ester; 2-benzyloxycarbonylmethylsulfanyl-6-hydroxy-pyrimidine-4-carboxylic-acid-methyl-ester; 3-(2-2-2-trichloro-1-isobutyrylamino)ethylthioureidobenzoic acid; ester of 2-diazo-1-naphthol-5-sulphone with 2-3-4-trihydroxybenzophenone; 4-5-dihydroxy-6-hydroxymethyl-2-methoxy-4H-pyran-3-yl-carbamic acid benzyl ester; diethyl-trans-1-2-cyclopropanedicarboxylate; 2-allyloxycarbonylmethylsulfanyl-6-hydroxy-pyrimidine-4-carboxylic acid methyl ester; 1-O-alpha-D-glucopyranosyl-D-fructose; methyl-2-2-4-chlorophenylsulfonylaminoacetylamino-2-phenylacetate; N-(2-hydroxy-4-oxo-4-phenylbut-2-enoyl)-2-methylquinoline-4-carbohydrazide; or DL-Djenkolic-acid.

5. The method of claim 4, wherein the composition is administered as a spray, an aerosol, or by way of an inhaler or nebulizer.

\* \* \* \* \*